US006297403B1

(12) United States Patent
Fritz-Langhals et al.

(10) Patent No.: US 6,297,403 B1
(45) Date of Patent: Oct. 2, 2001

(54) PROCESS FOR THE PREPARATION OF ALDEHYDES AND KETONES

(75) Inventors: Elke Fritz-Langhals, Ottobrun; Johannes Freudenreich, Munich, both of (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/478,280

(22) Filed: Jan. 5, 2000

Related U.S. Application Data

(62) Division of application No. 09/082,638, filed on May 21, 1998, now Pat. No. 6,023,000.

(30) Foreign Application Priority Data

Jun. 6, 1997 (DE) .............................................. 197 23 890

(51) Int. Cl.[7] ..................................................... C07C 45/36
(52) U.S. Cl. ........................... 568/320; 435/117; 435/147; 435/148; 568/357; 568/399; 568/431; 568/449; 568/470
(58) Field of Search ..................................... 435/117, 118, 435/120, 121, 122, 123, 125, 126, 147, 148; 568/320, 309, 426, 431, 357, 399, 322

(56) References Cited

U.S. PATENT DOCUMENTS 4,474,704 * 10/1984 Sawicki et al. ................... 260/429.7

FOREIGN PATENT DOCUMENTS

| 4445088 | 6/1996 | (DE) . |
| 59185787 | * 10/1984 | (JP) . |
| 0220653 | * 3/1996 | (JP) . |
| 9429425 | 12/1994 | (WO) . |
| 9429510 | 12/1994 | (WO) . |
| 9736039 | 10/1997 | (WO) . |
| 9736041 | 10/1997 | (WO) . |

OTHER PUBLICATIONS

Masui et al, J.Chem.Soc.,Chem.Commun.,479–480, 1983.*
Nooy et al, Synthesis, pp. 1153–1174, 1996.*
Potthast et al, J. of Molecular Catalysis, 108, pp. 5–9, 1996.*
Houben–Weyl, vol. E3, pp. 231–247 (1981).
Houben–Weyl, vol. VII/2a, pp. 688–699 (1984).
Organic Synthesis, Coll, vol. IV, 1961, p. 30–33.
Ishii et al, "Alkane Oxidation with Molecular Oxygen . . . ", J. Org. Chem., 1996, 61, pp. 4520–4526.
Potthast, et al, "Selective Enzymatic Oxidation of Aromatic . . . ", J. Org. Chem., 1995, 60, pp. 4320–4321.
Einhorn, et al, "Oxidation of Organic Substrates . . . ", Chem. Commun., 1997, pp. 447–448.
Enzyme List, International Enzyme Nomenclature, Committee of the International Union of Biochemistry and Molecular Biology, Academic Press, Inc.,1992, pp. 24–154.
Patent Abstract of Japan, vol. 015, No. 252 & JP 03081241A Agency of Ind. Science & Technol (1996).
Derwent Abstract (#96–301138[31]) Corresponding to DE 4445 088 (1996).

* cited by examiner

*Primary Examiner*—Sreeni Padmanabhan
(74) *Attorney, Agent, or Firm*—Collard & Roe, P.C.

(57) ABSTRACT

A process for the preparation of vinyl, alkynyl, aryl or heteroaryl aldehydes or vinyl, alkynyl, aryl or heteroaryl ketones includes reacting vinyl-, alkynyl-, aryl- and heteroarylmethyl and -methylene compounds with the aid of a mediator and an oxidant, wherein the mediator is selected from the group of the aliphatic, heterocyclic or aromatic NO, or NOH containing compounds.

11 Claims, No Drawings

PROCESS FOR THE PREPARATION OF ALDEHYDES AND KETONES

BACKGROUND OF THE INVENTION

This is a divisional of application Ser. No. 09/082,638 filed on May 21, 1998 now U.S. Pat. No. 6,023,000.

FIELD OF THE INVENTION

The present invention relates to a process for the preparation of aldehydes and ketones

THE PRIOR ART

Aldehydes and ketones are widely used in organic chemistry. For example, they are important precursors in the synthesis of heterocycles, or perfumes and dyestuffs.

A variety of processes are known for the preparation of aldehydes and ketones. For example, the formyl and the acyl group are successfully introduced directly into aromatic systems via electrophilic substitution reactions, which, however, are limited by the substitution rules. Aromatic ketones can also be synthesized via organometallic reactions. A disadvantage includes the necessity of using an anhydrous reaction medium. Another disadvantage is the use of toxic chemicals such as phosphorus oxychloride, carbon monoxide, zinc cyanide, mercury organyls and cadmium organyls.

Aldehydes and ketones may also be synthesized via oxidation reactions. An overview is given in the literature reviewed in Houben-Weyl, Vol. E3, p. 230 et seq., 1983, and Vol. 7/2a, p. 688 et seq. Customary oxidants are selenium dioxide, chromium trioxide, cerium(IV) ammonium nitrate in perchloric acid/nitric acid or manganese dioxide in concentrated sulfuric acid, 2,3-dichloro-5,6-dicyano-1,4-benzoquinone (DDQ) or iodine in DMSO. These oxidants, however, are also not very suitable for larger-scale syntheses due to their toxicity, the high costs or difficult handling. Moreover, most syntheses are complicated and yield the desired aldehyde only in moderate yield. In accordance with Org. Synth. Coll. Vol. IV, 1961, p. 31, 4-aminobenzaldehyde can be synthesized from nitrotoluene with the aid of polysulfide. Purification of the reaction product, which has a tendency to polymerize, is difficult and must be carried out rapidly, so that this process is unsuitable for larger amounts of substance.

When carrying out the oxidation with oxygen with addition of catalysts, not only are the desired aldehydes formed, but in most cases also the corresponding carboxylic acids (see Houben-Weyl, Vol. E3, p. 234 et seq., 1983). If this process is carried out with addition of N-hydroxyphthalimide and Co(II) or Co(III) compounds, even the starting material is fully oxidized to give the carboxylic acid (Ishii et al., J. Org. Chem. 1996, 61, 4520). Aromatic ketones are formed from alkylbenzenes with the aid of N-hydroxyphthalimide and acetaldehyde/oxygen in nonaqueous medium (Einhorn et al. in Chem. Commun. 1997, 447). The formation of aromatic aldehydes from the corresponding methyl aromatics with the aid of the enzyme laccase and ABTS (2,2'-azinobis(3-ethylbenzothiazoline-6-sulfonic acid) was described by Potthast in J. Org. Chem. 1995, 60, 4320. However, it was impossible to reproduce these results in independent experiments. Moreover, the laccase mentioned in the publication, by Mercian, which has an activity of $1.1 \times 10^4$ (IU/ml, based on the conversion of 4-hydroxymandelic acid as substrate), is not available. When attempting to reproduce the results, an available product, namely Mercian laccase with an activity of approx. 95 IU/ml, was employed at 100-fold concentration. A difficulty is that such high amounts of enzyme would completely exclude an applicability of the method for preparative purposes. Under these conditions, not even traces of an oxidation of 4-nitrotoluene was observed. When 3,4-dimethoxytoluene was used in the conversion, only 0.3% of 3,4-dimethoxybenzaldehyde were detected. Synthetic methods using ABTS are generally limited by the price of the compound, which is high.

There is therefore a demand for an inexpensive process which allows even sensitive aldehydes to be synthesized on a large scale. In particular, there is a need for a process in which water can be used as reaction medium.

SUMMARY OF THE INVENTION

The present invention relates to a process for the preparation of vinyl, alkynyl, aryl or heteroaryl aldehydes or vinyl, alkynyl, aryl or heteroaryl ketones from vinyl-, alkynyl-, aryl- and heteroarylmethyl and -methylene compounds with the aid of a mediator and an oxidant, wherein the mediator is selected from the group of the aliphatic, heterocyclic or aromatic NO, NOH or

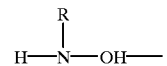

containing compounds.

The vinyl, alkynyl, aryl and heteroaryl aldehydes and vinyl, alkynyl, aryl and heteroaryl ketones are preferably compounds of the formula 1, and the vinyl-, alkynyl-, aryl- and heteroarylmethyl and -methylene compounds are preferably compounds of the formula 2

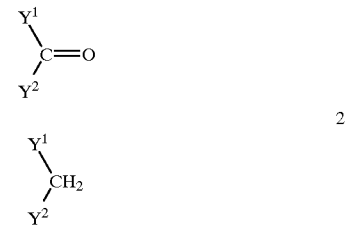

where $Y^1$ and $Y^2$ can be identical or different and are radicals having up to 20 C atoms and up to 6 rings and at least one of the radicals $Y^1$ or $Y^2$ is vinyl, alkynyl, aryl or heteroaryl, and $Y^1$ and $Y^2$ may also be part of a ring system.

$Y^1$ is preferably an aromatic or heteroaromatic ring or ring system having up to 6 rings and up to 20 Catoms, whose ring members can be replaced by O, S or N atoms, or an anthraquinonyl radical, it being possible for the aromatic or heteroaromatic radical $Y^1$ to be mono- to hexasubstituted, it being possible for the substituents to be identical or different and to have the meaning of OH, a linear, branched or cyclic $C_1$–$C_{12}$-alkyl radical, it being possible for adjacent alkyl groups to form a 5-, 6- or 7-membered ring via a methylene group, or a linear or branched $C_1$–$C_{12}$-oxyalkyl or thioalkyl radical, it being possible for adjacent substituents to form a 5-, 6- or 7-membered ring via a methylene group, a $H_2N$— or a linear or branched $C_1$–$C_{12}$—N-alkylamino, a linear or branched $C_1$–$C_{12}$—N,N-dialkyl-amino group, NC—, $O_2N$—, halogen, HOOC—, $HO_3S$—, OHC—, $H_2N$—COO—, $H_2N$—CO—, $H_2N$—CO—NH—, or a linear, branched or cyclic $C_1$–$C_{12}$—OCO—, $C_1$–$C_{12}$—OCO—, $C_1$–$C_{12}$—CO—, $C_1$–$C_{12}$—NHCO—, $C_1$–$C_{12}$—NHCONH—, ($C_1$–$C_{12}$)$_2$NCO—, $C_1$–$C_{12}$—CONH— group, or a linear or branched $C_1$–$C_{12}$—OSO$_2$—, $C_1$–$C_{12}$—NHSO$_2$—, or ($C_1$–$C_{12}$)$_2$N—SO$_2$— group, or a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-OSO$_2$— or phenyl-NH—SO$_2$— group whose phenyl radicals can be mono- to pentasubstituted, it being possible for the substituents to be identical or different and to have the meaning of OH, a linear, branched or cyclic $C_1$–$C_{12}$-alkyl radical, it being possible for adjacent alkyl groups to form a 5-, 6- or 7-membered ring via a methylene group, or of a linear or branched $C_1$–$C_{12}$-oxyalkyl or thioalkyl radical, it being possible for adjacent substituents to form a 5-, 6- or 7-membered ring via a methylene group, a H$_2$N— or a linear or branched $C_1$–$C_{12}$—N-alkylamino, a linear or branched $C_1$–$C_{12}$—N,N-dialkylamino group, NC—, O$_2$N—, halogen, HOOC—, HO$_3$S—, OHC—, H$_2$N—COO—, H$_2$N—CO—, H$_2$N—CO—NH—, or a linear, branched or cyclic $C_1$–$C_{12}$—OCO—, $C_1$–$C_{12}$—COO—, $C_1$–$C_{12}$—CO—, $C_1$–$C_{12}$—NHCO—, $C_1$–$C_{12}$—NHCONH—, ($C_1$–$C_{12}$)—NCO—, $C_1$–$C_{12}$—CONH—, or of a linear or branched $C_1$–$C_{12}$—OSO$_2$—, $C_1$–$C_{12}$—NH—SO$_2$— or ($C_1$–$C_{12}$)$_2$N—SO$_2$— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-OSO$_2$— or phenyl-NH—SO$_2$— group or an optionally mono- to trisubstituted vinyl radical or optionally substituted ethynyl radical, in which the substituents can be identical or different and have the meaning of hydrogen, linear, branched or cyclic $C_1$–$C_{12}$-alkyl radical where one or more methylene groups can be replaced individually by CHOH, CO, O, S, NH or by a linear or branched $C_1$–$C_{12}$—N-alkylamine radical, or in which the vinyl group forms part of a ring or ring system, and $Y^2$ is hydrogen, linear, branched or cyclic $C_1$–$C_{12}$-alkyl radical where one or more methylene groups can be replaced individually by CHOH, CO, O, S, NH or by a linear or branched $C_1$–$C_{12}$—N-alkylamine radical, or an aromatic or heteroaromatic ring or ring system having up to 6 rings and up to 20 C atoms, whose ring members can be replaced by O, S or N atoms, or anthraquinonyl radical, or an optionally mono- to trisubstituted vinyl radical or optionally substituted ethynyl radical, in which the substituents can be identical or different and have the meaning of hydrogen, linear, branched or cyclic $C_1$–$C_{12}$-alkyl radical where one or more methylene groups can be replaced individually by CHOH, CO, O, S, NH or by a linear or branched $C_1$–$C_{12}$—N-alkylamine radical, or in which the vinyl group forms part of a ring or ring system.

Equally preferred are compounds in which the radicals $Y^1$ and $Y^2$ are linked via a methylene group or an ether group or via an amino group which is optionally substituted by a linear, branched or cyclic $C_1$–$C_{12}$-alkyl radical.

Especially preferably, $Y^1$ is a 5-, 6- or 7-membered aromatic or heteroaromatic ring which can be fused to one or two further aromatic rings and where one to four C atoms can be replaced by O, S or N atoms, or an anthraquinonyl radical, it being possible for $Y^1$ to be mono- to tetrasubstituted, it being possible for the substituents to be identical or different and to have the meaning of OH, a linear, branched or cyclic $C_1$–$C_6$-alkyl radical, it being possible for adjacent alkyl groups to form a 5- or 6-membered ring via a methylene group, or a linear or branched $C_1$–$C_6$-oxyalkyl or -thioalkyl radical, it being possible for adjacent substituents to form a 5- or 6-membered ring via a methylene group, of a H$_2$N—, or a linear or branched $C_1$–$C_6$—N-alkylamino, a linear or branched $C_1$–$C_3$—N,N-dialkylamino group, NC—, O$_2$N—, halogen, HOOC—, HO$_3$S—, OHC—, H$_2$N—COO—, H$_2$N—CO—, H$_2$N—CO—NH—, or a linear, branched or cyclic $C_1$–$C_6$—OCO—, $C_1$–$C_6$—COO—, $C_1$–$C_6$—CO—, $C_1$–$C_6$—NHCO—, $C_1$–$C_6$—NHCONH—, ($C_1$–$C_6$)$_2$NCO—, $C_1$–$C_6$—CONH—, or of a linear or branched $C_1$–$C_6$—OSO$_2$—, $C_1$–$C_6$—NH—SO$_2$— or ($C_1$–$C_3$)$_2$N—SO$_2$— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-OSO$_2$— or phenyl-NH—SO$_2$— group, it being possible for the phenyl radicals to be mono- to trisubstituted, it being possible for the substituents to be identical or different and to have the meaning of OH, a linear, branched or cyclic $C_1$–$C_6$-alkyl radical, it being possible for adjacent alkyl groups to form a 5- or 6-membered ring via a methylene group, or a linear or branched $C_1$–$C_6$-oxyalkyl or -thioalkyl radical, it being possible for adjacent substituents to form a 5- or 6-membered ring via a methylene group, of a H$_2$N—, or a linear or branched $C_1$–$C_6$—N-alkylamino, a linear or branched $C_1$–$C_3$—N,N-dialkylamino group, NC—, O$_2$N—, halogen, HOOC—, HO$_3$S—, OHC—, H$_2$N—COO—, H$_2$N—CO—, H$_2$N—CO—NH—, or a linear, branched or cyclic $C_1$–$C_6$—OCO—, $C_1$–$C_6$—COO—, $C_1$–$C_6$—CO—, $C_1$–$C_6$—NHCO—, $C_1$–$C_6$—NHCONH—, ($C_1$–$C_6$)$_2$NCO—, $C_1$–$C_6$—CONH—, or of a linear or branched $C_1$–$C_6$—OSO$_2$—, $C_1$–$C_6$—NH—SO$_2$—or ($C_1$–$C_3$)$_2$N—SO$_2$— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-OSO$_2$— or phenyl-NH—SO— group, or an optionally mono- to trisubstituted vinyl radical or optionally substituted ethynyl radical, it being possible for the substituents to be identical or different and to be hydrogen or linear, branched, or cyclic $C_1$–$C_6$-alkyl radical where one or two methylene groups can be replaced individually by —CHOH, CO, O, S, NH or by a linear or branched $C_1$–$C_6$—N-alkylamine radical, or in which the vinyl group forms part of a 5- or 6-membered ring or of a ring system, and $Y^2$ is hydrogen or linear, branched or cyclic $C_1$–$C_6$-alkyl radical where one or two methylene groups can be replaced individually by —CHOH, CO, O, S, NH or by a linear or branched $C_1$–$C_6$—N-alkylamine radical, or a 5-, 6- or 7-membered aromatic or heteroaromatic ring which can be fused to one or two further aromatic rings and where one to four C atoms can be replaced by O, S or N atoms, or an anthraquinonyl radical, or an optionally mono- to trisubstituted vinyl radical, or an optionally substituted ethynyl radical, it being possible for the substituents to be identical or different and to be hydrogen or linear, branched, or cyclic $C_1$–$C_6$-alkyl radical where one or two methylene groups can be replaced individually by —CHOH, CO, O, S, NH or by a linear or branched $C_1$–$C_6$—N-alkylamine radical, or in which the vinyl group forms part of a 5- or 6-membered ring or of a ring system.

Equally especially preferred are compounds where the radicals $Y^1$ and $Y^2$ are linked via a methylene group or an ether group or via an amino group which is optionally substituted by a linear, branched or cyclic $C_1$–$C_6$-alkyl radical.

Very especially preferably, $Y^1$ is phenyl, naphthyl, anthryl, phenanthryl, azulenyl, anthraquinonyl, furyl, pyrrolyl, thienyl, benzofuranyl, isobenzofuranyl, benzothiyl, isobenzothienyl, indolyl, isoindolyl, indolizinyl, pyrazolyl, imidazolyl, oxazolyl, thiazolyl, isoxazolyl, isothiazolyl, indazolyl, carbazolyl, benzotriazolyl, purinyl, pyridyl, pyridazinyl, pyrimidyl, pyrazinyl, quinolinyl, isoquinolinyl, quinoxalinyl, quinazolinyl, cinnolinyl, phenanthridinyl, acridinyl, 1,10-phenanthrolinyl, phenazinyl, phenothiazinyl, phenoxazinyl, it being possible for $Y^1$ to be mono- to trisubstituted, it being possible for the substituents to be identical or different and to have the meaning of OH, a linear $C_1$–$C_6$-alkyl radical, it being possible for adjacent alkyl groups to form a 5- or 6-membered ring via a methylene group, or of a linear $C_1$–$C_6$-oxyalkyl radical, it being possible for adjacent substituents to form a 5- or 6-membered ring via a methylene group, a $H_2N$—, or a linear $C_1$–$C_6$—N-alkylamino, a linear $C_1$–$C_3$—N,N-dialkylamino group, NC—, $O_2N$—, halogen, HOOC—, $HO_3S$—, OHC—, $H_2N$—COO—, $H_2N$—CO—, $H_2N$—CO—NH—, or a linear $C_1$–$C_4$—OCO—, $C_1$–$C_4$—COO—, $C_1$–$C_4$—CO—, $C_1$–$C_4$—NHCO—, $(C_1$–$C_4)_2$NCO—, $C_1$–$C_4$—CONH—, $C_1$–$C_4$—NHCONH—, or $C_1$–$C_4$—$OSO_2$—, $C_1$–$C_4$—NH—$SO_2$— or $(C_1$–$C_3)_2$N—$SO_2$— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-$OSO_2$— or phenyl-NH—$SO_2$— group, it being possible for the phenyl radicals to be mono- to trisubstituted, it being possible for the substituents to be identical or different and to have the meaning of OH, a linear $C_1$–$C_6$ alkyl radical, it being possible for adjacent alkyl groups to form a 5- or 6-membered ring via a methylene group, or of a linear $C_1$–$C_6$-oxyalkyl radical, it being possible for adjacent substituents to form a 5- or 6-membered ring via a methylene group, a $H_2N$—, or a linear $C_1$–$C_6$—N-alkylamino, a linear $C_1$–$C_3$—N,N-dialkylamino group, NC—, $O_2N$—, halogen, HOOC—, $HO_3S$—, OHC—, $H_2N$—COO—, $H_2N$—CO—, $H_2N$—CO—NH—, or a linear $C_1$–$C_4$—OCO—, $C_1$–$C_4$—COO—, $C_1$–$C_4$—CO—, $C_1$–$C_4$—NHCO—, $(C_1$–$C_4)_2$NCO—, $C_1$–$C_4$—CONH—, $C_1$–$C_4$—NHCONH—, or $C_1$–$C_4$—$OSO_2$—, $C_1$–$C_4$—NH—$SO_2$— or $(C_1$–$C_4)_2$N—$SO_2$— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-$OSO_2$— or phenyl-NH—$SO_2$— group or an optionally mono- to trisubstituted vinyl radical, or optionally substituted ethynyl radical, in which the substituents can be identical or different and are hydrogen or linear $C_1$–$C_4$-alkyl radical where one or two methylene groups can be replaced individually by CHOH, CO, O, S, NH or by a linear or branched $C_1$–$C_6$—N-alkylamine radical, or in which the vinyl group forms part of a 5- or 6-membered ring or of a ring system, and $Y^2$ is hydrogen or a linear $C_1$–$C_6$-alkyl radical where one or two methylene groups can be replaced individually by CHOH, CO, O, S, NH or by a linear or branched $C_1$–$C_6$— N-alkylamine radical, or is phenyl, naphthyl, anthryl, phenanthryl, azulenyl, anthraquinonyl, furyl, pyrrolyl, thienyl, benzofuranyl, isobenzofuranyl, benzothiyl, isobenzothienyl, indolyl, isoindolyl, indolizinyl, pyrazolyl, imidazolyl, oxazolyl, thiazolyl, isoxazolyl, isothiazolyl, indazolyl, carbazolyl, benzotriazolyl, purinyl, pyridyl, pyridazinyl, pyrimidyl, pyrazinyl, quinolinyl, isoquinolinyl, quinoxalinyl, quinazolinyl, cinnolinyl, phenanthridinyl, acridinyl, 1,10-phenanthrolinyl, phenazinyl, phenothiazinyl, phenoxazinyl, or an optionally mono- to trisubstituted vinyl radical, or optionally substituted ethynyl radical, in which the substituents can be identical or different and are hydrogen or linear $C_1$–$C_6$-alkyl radical where one or two methylene groups can be replaced individually by CHOH, CO, O, S, NH or by a linear or branched $C_1$–$C_6$—N-alkylamine radical, or in which the vinyl group forms part of a 5- or 6-membered ring or of a ring system.

Examples of such compounds are toluene, ethylbenzene, propylbenzene, ortho-, meta- and para-xylene, 3,4-dimethoxytoluene, 4-methylaniline, diphenylmethane, propene, 2-butene, 1-octene and 3-phenyl-1-propyne.

Equally very especially preferred are compounds in which the radicals $Y^1$ and $Y^2$ are linked via a methylene group or an ether group or via an amino group which is optionally substituted by a methyl, ethyl, n- or isopropyl radical, the linkage resulting in 5- or 6-membered rings.

Examples are cyclohexene, indane, indene, 1,2,3,4-tetrahydronaphthalene, 6-methoxy-1,2,3,4-tetrahydronaphthalene, 9,10-dihydrophenanthrene, 3,4-dihydro-2H-pyrane, 1,2,3,4-tetrahydroquinoline, 1,2,3,4-tetrahydroisoquinoline.

The mediator used is preferably at least one compound selected from the group of the aliphatic, cycloaliphatic, heterocyclic or aromatic compounds which contains at least one N-hydroxyl, oxime, nitroso, nitroxide or N-oxide function.

Examples of such compounds are the compounds of the formula I, II, III or IV, mentioned below, the compounds of the formulae II, III and IV being preferred and the compounds of the formulae III and IV being especially preferred.

Compounds of the general formula I are:

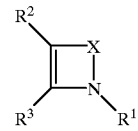

I where X is one of the following groups:

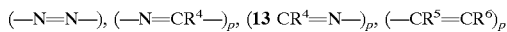

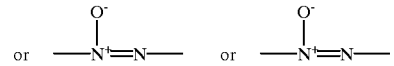

and p equals 1 or 2, it being possible for the radicals $R^1$ to $R^6$ to be identical or different and independently of one another to represent one of the following groups: hydrogen, halogen, hydroxyl, formyl, carboxyl and the salts and esters thereof, amino, nitro, $C_1$–$C_{12}$-alkyl, $C_1$–$C_6$-alkyloxy, carbonyl-$C_1$–$C_6$-alkyl, phenyl, sulfono, esters and salts thereof, sulfamoyl, carbamoyl, phospho, phosphono, phosphonooxy and their salts and esters, and it furthermore being possible for the amino, carbamoyl and sulfamoyl groups of the radicals $R^1$ to $R^6$ to be unsubstituted or to be mono- or disubstituted by hydroxyl, $C_1$–$C_3$-alkyl or $C_1$–$C_3$-alkoxy, and it being possible for the radicals $R^2$ and $R^3$ to form a joint group —A—, where —A— represents one of the following groups:

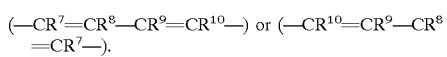

The radicals $R^7$ to $R^{10}$ can be identical or different and independently of one another can represent one of the following groups: hydrogen, halogen, hydroxyl, formyl, carboxyl and the salts and esters thereof, amino, nitro, $C_1$–$C_{12}$-alkyl, $C_1$–$C_6$-alkyloxy, carbonyl-$C_1$–$C_6$-alkyl, phenyl sulfono, esters and salts thereof, sulfamoyl, carbamoyl, phospho, phosphono, phosphonooxy and their salts and esters, and it furthermore being possible for the amino, carbamoyl and sulfamoyl groups of the radicals $R^7$ to $R^{10}$ to be unsubstituted or to be mono- or disubstituted by hydroxyl, $C_1$–$C_3$-alkyl or $C_1$–$C_3$-alkoxy, and it being possible for the $C_1$–$C_{12}$-alkyl, $C_1$–$C_6$-alkyloxy, carbonyl-$C_1$–$C_6$-alkyl, phenyl or aryl groups of the radicals $R^7$ to $R^{10}$ to be unsubstituted or furthermore to be mono- or polysubstituted by the radical $R^{11}$, and it being possible for the radical $R^{11}$ to represent one of the following groups: hydrogen, halogen, hydroxyl, formyl, carboxyl and their salts and esters, amino, nitro, $C_1$–$C_{12}$-alkyl, $C_1$–$C_6$-alkyloxy, carbonyl-$C_1$–$C_6$-alkyl, phenyl, aryl, and their esters and salts, and it being possible for the carbamoyl, sulfamoyl and amino groups of the radical $R^{11}$ to be unsubstituted or furthermore to be mono- or disubstituted by the radical $R^{12}$, and it being possible for the radical $R^{12}$ to represent one of the following groups: hydrogen, hydroxyl, formyl, carboxyl and their salts and esters, amino, nitro, $C_1$–$C_{12}$-alkyl, $C_1$–$C_6$-alkyloxy, carbonyl-$C_1$–$C_6$-alkyl, phenyl or aryl.

Examples of the abovementioned compounds are:
1-hydroxy-1,2,3-triazole-4,5-dicarboxylic acid
1-phenyl-1H-1,2,3-triazole-3-oxide
5-chloro-1-phenyl-1H-1,2,3-triazole-3-oxide
5-methyl-1-phenyl-1H-1,2,3-triazole-3-oxide
4-(2,2-dimethylpropanoyl)-1-hydroxy-1H-1,2,3-triazole
4-hydroxy-2-phenyl-2H-1,2,3-triazole-1-oxide
2,4,5-triphenyl-2H-1,2,3-triazole-1-oxide
1-benzyl-1H-1,2,3-triazole-3-oxide
1-benzyl-4-chloro-1H-1,2,3-triazole-3-oxide
1-benzyl-4-bromo-1H-1,2,3-triazole-3-oxide
1-benzyl-4-methoxy-1H-1,2,3-triazole-3-oxide Compounds of the general formula II are:

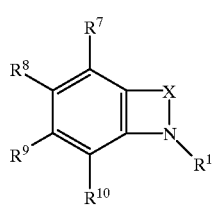

II where X is one of the following groups:

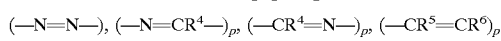

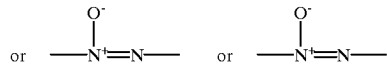

and p equals 1 or 2.

The radicals $R^1$ and $R^4$ to $R^{10}$ can be identical or different and independently of one another can represent one of the following groups: hydrogen, halogen, hydroxyl, formyl, carboxyl and the salts and esters thereof, anino, nitro, $C_1$–$C_{12}$-alkyl, $C_1$–$C_6$-alkyloxy, carbonyl-$C_1$–$C_6$-alkyl, phenyl, aryl, sulfono, esters and salts thereof, sulfamoyl, carbamoyl, phospho, phosphono, phosphonooxy and their salts and esters, and it furthermore being possible for the amino, carbamoyl and sulfamoyl groups of the radicals $R^1$ and $R^4$ to $R^{10}$ to be unsubstituted or to be mono- or disubstituted by hydroxyl, $C_1$–$C_3$-alkyl or $C_1$–$C_3$-alkoxy, and it being possible for the $C_1$–$C_{12}$-alkyl, $C_1$–$C_6$-alkyloxy, carbonyl-$C_1$–$C_6$-alkyl, phenyl, aryl and aryl-$C_1$–$C_6$-alkyl groups of the radicals $R^1$ and $R^4$ to $R^{10}$ to be unsubstituted or furthermore to be mono- or polysubstituted by the radical $R^{12}$, and it being possible for the radical $R^{12}$ to represent one of the following groups: hydrogen, halogen, hydroxyl, formyl, carboxyl and their salts and esters, amino, nitro, $C_1$–$C_{12}$-alkyl, $C_1$–$C_6$-alkyloxy, carbonyl-$C_1$–$C_6$-alkyl, phenyl, aryl, sulfono, sulfeno, sulfino and their esters and salts, and it being possible for the carbamoyl, sulfamoyl and amino groups of the radical $R^{12}$ to be unsubstituted or furthermore to be mono- or disubstituted by the radical $R^3$, and it being possible for the radical $R^{13}$ to represent one of the following groups: hydroxyl, hydroxyl, formyl, carboxyl and their salts and esters, amino, nitro, $C_1$–$C_{12}$-alkyl, $C_1$–$C_6$-alkyloxy, carbonyl-$C_1$–$C_6$-alkyl, phenyl, aryl.

Examples of the abovementioned compounds are:
1-hydroxybenzimidazoles
1-hydroxybenzimidazole-2-carboxylic acid
1-hydroxybenzimidazole
2-methyl-1-hydroxybenzimidazole
2-phenyl-1-hydroxybenzimidazole
1-hydroxyindoles
2-phenyl-1-hydroxyindole Substances of the general formula III are:

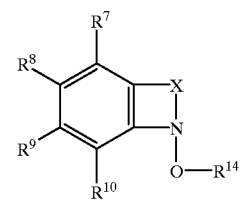

III where X is one of the following groups:

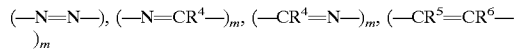

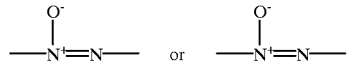

and m equals 1 or 2.

What has been said above for the radicals $R^7$ to $R^{10}$ and $R^4$ to $R^6$ also applies here.

$R^{14}$ can be: hydrogen, $C_1$–$C_{10}$-alkyl or $C_1$–$C_{10}$-alkylcarbonyl whose $C_1$–$C_{10}$-alkyl and $C_1$–$C_{10}$-alkylcarbonyl can be unsubstituted or mono- or polysubstituted by a radical $R^{15}$, it being possible for $R^{15}$ to represent one of the following groups: hydrogen, halogen, hydroxyl, formyl, carboxyl and salts and esters thereof, amino, nitro, $C_1$–$C_{12}$-alkyl, $C_1$–$C_6$-alkyloxy, carbonyl-$C_1$–$C_6$-alkyl, phenyl, sulfono, their esters and salts, sulfamoyl, carbamoyl, phospho, phosphono, phosphonooxy and their salts and esters, it being possible for the amino, carbamoyl and sulfamoyl groups of the radical $R^{15}$ furthermore to be unsubstituted or mono- or disubstituted by hydroxyl, $C_1$–$C_3$-alkyl or $C_1$–$C_3$-alkoxy.

Particularly preferred amongst the substances of the formula III are derivatives of 1-hydroxybenzotriazole and of the tautomeric benzotriazole 1-oxide, and their esters and salts (compounds of the formula IV)

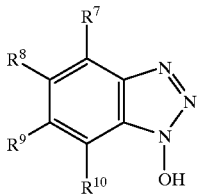

IV

The radicals $R^7$ to $R^{10}$ can be identical or different and independently of one another represent one of the following groups: hydrogen, halogen, hydroxyl, formyl, carboxyl and salts and esters thereof, amino, nitro, $C_1$–$C_{12}$-alkyl, $C_1$–$C_6$-alkyloxy, carbonyl-$C_1$–$C_6$-alkyl, phenyl, sulfono, esters and salts thereof, sulfamoyl, carbamoyl, phospho, phosphono, phosphonooxy and their salts and esters, it furthermore being possible for the amino, carbamoyl and sulfamoyl groups of the radicals $R^7$ to $R^{10}$ to be unsubstituted or to be mono- or disubstituted by hydroxyl, $C_1$–$C_3$-alkyl or $C_1$–$C_3$-alkoxy and it being possible for the $C_1$–$C_{12}$-alkyl, $C_1$–$C_6$-alkyloxy, carbonyl-$C_1$–$C_6$-alkyl, phenyl and aryl groups of the radicals $R^7$ to $R^{10}$ to be unsubstituted or furthermore mono- or polysubstituted by the radical $R^{16}$, and it being possible for the radical $R^{16}$ to represent one of the following groups: hydrogen, halogen, hydroxyl, formyl, carboxyl and their salts and esters, amino, nitro, $C_1$–$C_{12}$-alkyl, $C_1$–$C_6$-alkyloxy, carbonyl-$C_1$–$C_6$-alkyl, phenyl, aryl, sulfono, sulfeno, sulfino and also their esters and salts, and it being possible for the carbamoyl, sulfamoyl and amino groups of the radical $R^{16}$ to be unsubstituted or furthermore mono- or disubstituted by the radical $R^{17}$ and it being possible for the radical $R^{17}$ to represent one of the following groups: hydrogen, hydroxyl, formyl, carboxyl and their salts and esters, amino, nitro, $C_1$–$C_{12}$-alkyl, $C_1$–$C_6$-alkyloxy, carbonyl-$C_1$–$C_6$-alkyl, phenyl, aryl.

Examples of the abovementioned compounds are:

1H-hydroxybenzotriazoles 1-hydroxybenzotriazole
1-hydroxybenzotriazole, sodium salt.
1-hydroxybenzotriazole, potassium salt
1-hydroxybenzotriazole, lithium salt
1-hydroxybenzotriazole, ammonium salt
1-hydroxybenzotriazole, calcium salt
1-hydroxybenzotriazole, magnesium salt
1-hydroxybenzotriazole-6-sulfonic acid
1-hydroxybenzotriazole-6-sulfonic acid, monosodium salt
1-hydroxybenzotriazole-6-carboxylic acid
1-hydroxybenzotriazole-6-N-phenylcarboxamide
5-ethoxy-6-nitro-1-hydroxybenzotriazole
4-ethyl-7-methyl-6-nitro-1-hydroxybenzotriazole
2,3-bis(4-ethoxyphenyl)-4,6-dinitro-2,3-dihydro-1-hydroxybenzotriazole
2,3-bis(2-bromo-4-methylphenyl)-4,6-dinitro-2,3-dihydro-1-hydroxybenzotriazole
2,3-bis(4-bromophenyl)-4,6-dinitro-2,3-dihydro-1-hydroxybenzotriazole
2,3-bis(4-carboxyphenyl)-4,6-dinitro-2,3-dihydro-1-hydroxybenzotriazole
4,6-bis(trifluoromethyl)-1-hydroxybenzotriazole
5-bromo-1-hydroxybenzotriazole
6-bromo-1-hydroxybenzotriazole
4-bromo-7-methyl-1-hydroxybenzotriazole
5-bromo-7-methyl-6-nitro-1-hydroxybenzotriazole
4-bromo-6-nitro-1-hydroxybenzotriazole
6-bromo-4-nitro-1-hydroxybenzotriazole
4-chloro-1-hydroxybenzotriazole
5-chloro-1-hydroxybenzotriazole
6-chloro-1-hydroxybenzotriazole
6-chloro-5-isopropyl-1-hydroxybenzotriazole
5-chloro-6-methyl-1-hydroxybenzotriazole
6-chloro-5-methyl-1-hydroxybenzotriazole
4-chloro-7-methyl-6-nitro-1-hydroxybenzotriazole
4-chloro-5-methyl-1-hydroxybenzotriazole
5-chloro-4-methyl-1-hydroxybenzotriazole
4-chloro-6-nitro-1-hydroxybenzotriazole
6-chloro-4-nitro-1-hydroxybenzotriazole
7-chloro-1-hydroxybenzotriazole
6-diacetylamino-1-hydroxybenzotriazole
2,3-dibenzyl-4,6-dinitro-2,3-dihydro-1-hydroxybenzotriazole
4,6-dibromo-1-hydroxybenzotriazole
4,6-dichloro-1-hydroxybenzotriazole
5,6-dichloro-1-hydroxybenzotriazole
4,5-dichloro-1-hydroxybenzotriazole
4,7-dichloro-1-hydroxybenzotriazole
5,7-dichloro-6-nitro-1-hydroxybenzotriazole
5,6-dimethoxy-1-hydroxybenzotriazole
2,3-di-[2]naphthyl-4,6-dinitro-2,3-dihydro-1-hydroxybenzotriazole
4,6-dinitro-1-hydroxybenzotriazole
4,6-dinitro-2,3-diphenyl-2,3-dihydro-1-hydroxybenzotriazole
4,6-dinitro-2,3-di-p-tolyl-2,3-dihydro-1-hydroxybenzotriazole
5-hydrazino-7-methyl-4-nitro-1-hydroxybenzotriazole
5,6-dimethyl-1-hydroxybenzotriazole
4-methyl-1-hydroxybenzotriazole
5-methyl-1-hydroxybenzotriazole
6-methyl-1-hydroxybenzotriazole
5-(1-methylethyl)-1-hydroxybenzotriazole
4-methyl-6-nitro-1-hydroxybenzotriazole
6-methyl-4-nitro-1-hydroxybenzotriazole
5-methoxy-1-hydroxybenzotriazole
6-methoxy-1-hydroxybenzotriazole
7-methyl-6-nitro-1-hydroxybenzotriazole
4-nitro-1-hydroxybenzotriazole
6-nitro-1-hydroxybenzotriazole
6-nitro-4-phenyl-1-hydroxybenzotriazole
5-phenylmethyl-1-hydroxybenzotriazole
4-trifluoromethyl-1-hydroxybenzotriazole
5-trifluoromethyl-1-hydroxybenzotriazole
6-trifluoromethyl-1-hydroxybenzotriazole
4,5,6,7-tetrachloro-1-hydroxybenzotriazole
4,5,6,7-tetrafluoro-1-hydroxybenzotriazole
6-tetrafluoroethyl-1-hydroxybenzotriazole
4,5,6-trichloro-1-hydroxybenzotriazole
4,6,7-trichloro-1-hydroxybenzotriazole
6-sulfamido-1-hydroxybenzotriazole
6-N,N-diethylsulfamido-1-hydroxybenzotriazole
6-N-methylsulfamido-1-hydroxybenzotriazole
6-(1H-1,2,4-triazol-1-ylmethyl)-1-hydroxybenzotriazole
6-(5,6,7,8-tetrahydroimidazo[1,5-a]pyridin-5-yl)-1-hydroxybenzotriazole
6-(phenyl-1H-1,2,4-triazol-1-ylmethyl)-1-hydroxybenzotriazole
6-[(5-methyl-1H-imidazo-1-yl)phenylmethyl]-1-hydroxybenzotriazole
6-[(4-nethyl-1H-imidazo-1-yl)phenylmethyl]-1-hydroxybenzotriazole
6-[(2-methyl-1H-imidazo-1-yl)phenylmethyl]-1-hydroxybenzotriazole 6-(1H-1-midazol-1-ylphenylmethyl)-1-hydroxybenzotriazole
5-(1H-imidazol-1-ylphenylmethyl)-1-hydroxybenzotriazole
6-[1-(1H-imidazol-1-yl)ethyl]-1-hydroxybenzotriazole monohydrochloride 3H-benzotriazole 1-oxides 3H-benzotriazole 1-oxide
6-acetyl-3H-benzotriazole 1-oxide
5-ethoxy-6-nitro-3H-benzotriazole 1-oxide
4-ethyl-7-methyl-6-nitro-3H-benzotriazole 1-oxide
6-amino-3,5-dimethyl-3H-benzotriazole 1-oxide
6-amino-3-methyl-3H-benzotriazole 1-oxide
5-bromo-3H-benzotriazole 1-oxide
6-bromo-3H-benzotriazole 1-oxide
4-bromo-7-methyl-3H-benzotriazole 1-oxide
5-bromo-4-chloro-6-nitro-3H-benzotriazole 1-oxide
4-bromo-6-nitro-3H-benzotriazole 1-oxide
6-bromo-4-nitro-3H-benzotriazole 1-oxide
5-chloro-3H-benzotriazole 1-oxide
6-chloro-3H-benzotriazole 1-oxide
4-chloro-6-nitro-3H-benzotriazole 1-oxide
4,6-dibromo-3H-benzotriazole 1-oxide
4,6-dibromo-3-methyl-3H-benzotriazole 1-oxide
4,6-dichloro-3H-benzotriazole 1-oxide
4,7-dichloro-3H-benzotriazole 1-oxide
5,6-dichloro-3H-benzotriazole 1-oxide
4,6-dichloro-3-methyl-3H-benzotriazole 1-oxide
5,7-dichloro-6-nitro-3H-benzotriazole 1-oxide
3,6-dimethyl-6-nitro-3H-benzotriazole 1-oxide
3,5-dimethyl-6-nitro-3H-benzotriazole 1-oxide
3-methyl-3H-benzotriazole 1-oxide
5-methyl-3H-benzotriazole 1-oxide
6-methyl-3H- benzotriazole 1-oxide
6-methyl-4-nitro-3H-benzotriazole 1-oxide
6-methyl-4-nitro-3H-benzotriazole 1-oxide
5-chloro-6-nitro-3H-benzotriazole 1-oxide 2H-benzotriazole 1-oxides 2-(4-acetoxyphenyl)-2H-benzotriazole 1-oxide
6-acetylamino-2-phenyl-2H-benzotriazole 1-oxide
2-(4-ethylphenyl)-4, 6-dinitro-2H-benzotriazole 1-oxide
2-(3-aminophenyl)-2H-benzotriazole 1-oxide
2-(4-aminophenyl)-2H-benzotriazole 1-oxide
6-amino-2-phenyl-2H-benzotriazole 1-oxide
5-bromo-4-chloro-6-nitro-2-phenyl-2H-benzotriazole 1-oxide
2-(4-brominophenyl)-2H-benzotriazole 1-oxide
5-bromo-2-phenyl-2H-benzotriazole 1-oxide
6-bromo-2-phenyl-2H-benzotriazole 1-oxide
2-(4-bromophenyl)-4,6-dinitro-2H-benzotriazole 1-oxide
2-(4-bromophenyl)-6-nitro-2H-benzotriazole 1-oxide
5-chloro-2-(2-chlorophenyl)-2H-benzotriazole 1-oxide
5-chloro-2-(3-chlorophenyl)-2H-benzotriazole 1-oxide
5-chloro-2-(2-chlorophenyl)-2H-benzotriazole 1-oxide
5-chloro-2-(3-chlorophenyl)-2H-benzotriazole 1-oxide
5-chloro-2-(2,4-dibromophenyl)-2H-benzotriazole 1-oxide
5-chloro-2-(2,5-dimethylphenyl)-2H-benzotriazole 1-oxide
5-chloro-2-(4-nitrophenyl)-2H-benzotriazole 1-oxide
5-chloro-6-nitro-2-phenyl-2H-benzotriazole 1-oxide
2-[4-(4-chloro-3-nitrophenylazo)-3-nitrophenyl]-4,6-dinitro-2H-benzotriazole 1-oxide
2-(3-chloro-4-nitrophenyl)-4,6-dinitro-2H-benzotriazole 1-oxide
2-(4-chloro-3-nitrophenyl)-4,6-dinitro-2H-benzotriazole 1-oxide
4-chloro-6-nitro-2-p-tolyl-2H-benzotriazole 1-oxide
5-chloro-6-nitro-2-p-tolyl-2H-benzotriazole 1-oxide
6-chloro-4-nitro-2-p-tolyl-2H-benzotriazole 1-oxide
2-(2-chlorophenyl)-2H-benzotriazole 1-oxide
2-(3-chlorophenyl)-2H-benzotriazole 1-oxide
2-(4-chlorophenyl)-2H-benzotriazole 1-oxide
5-chloro-2-phenyl-2H-benzotriazole 1-oxide
2-[4-(4-chlorophenylazo)-3-nitrophenyl]-4,6-dinitro-2H-benzotriazole 1-oxide
2-(2-chlorophenyl)-4,6-dinitro-2H-benzotriazole 1-oxide
2-(3-chlorophenyl)-4,6-dinitro-2H-benzotriazole 1-oxide
2-(4-chlorophenyl)-4,6-dinitro-2H-benzotriazole 1-oxide
2-{4-[N'-(3-chlorophenyl)hydrazino]-3-nitrophenyl}-4,6-dinitro-2H-benzotriazole 1-oxide
2-{4-[N'-(4-chlorophenyl)hydrazino]-3-nitrophenyl}-4,6-dinitro-2H-benzotriazole 1-oxide
2-(2-chlorophenyl)-6-methyl-2H-benzotriazole 1-oxide
2-(3-chlorophenyl)-6-methyl-2H-benzotriazole 1-oxide
2-(4-chlorophenyl)-6-methyl-2H-benzotriazole 1-oxide
2-(3-chlorophenyl)-6-nitro-2H-benzotriazole 1-oxide
2-(4-chlorophenyl)-6-nitro-2H-benzotriazole 1-oxide
2-(4-chlorophenyl)-6-picrylazo-2H-benzotriazole 1-oxide
5-chloro-2-(2,4,5-trimethylphenyl)-2H-benzotriazole 1-oxide
4,5-dibromo-6-nitro-2-p-tolyl-2H-benzotriazole 1-oxide
4,5-dichloro-6-nitro-2-phenyl-2H-benzotriazole 1-oxide
4,5-dichloro-6-nitro-2-p-tolyl-2H-benzotriazole 1-oxide
4,7-dichloro-6-nitro-2-p-tolyl-2H-benzotriazole 1-oxide
4,7-dimethyl-6-nitro-2-phenyl-2H-benzotriazole 1-oxide
2-(2,4-dimethylphenyl)-4,6-dinitro-benzotriazole 1-oxide
2-(2,5-dimethylphenyl)-4,6-dinitro-2H-benzotriazole 1-oxide
2-(2,4-dimethylphenyl)-6-nitro-2H-benzotriazole 1-oxide
2-(2,5-dimethylphenyl)-6-nitro-2H-benzotriazole 1-oxide
4,6-dinitro-2-[3-nitro-4-(N'-phenylhydrazino)phenyl]-2H-enzotriazole 1-oxide
4,6-dinitro-2-[4-nitro-4-(N'-phenylhydrazino)phenyl]-2H-benzotriazole 1-oxide
4,6-dinitro-2-phenyl-2H-benzotriazole 1-oxide
2-(2,4-dinitrophenyl)-4,6-dinitro-2H-benzotriazole 1-oxide
2-(2,4-dinitrophenyl)-6-nitro-2H-benzotriazole 1-oxide
4,6-dinitro-2-o-tolyl-2H-benzotriazole 1-oxide
4,6-dinitro-2-p-tolyl-2H-benzotriazole 1-oxide
4,6-dinitro-2-(2,4,5-trimethylphenyl)-2H-benzotriazole 1-oxide
2-(4-methoxyphenyl)-2H-benzotriazole 1-oxide
2-(4-methoxyphenyl)-6-methyl-2H-benzotriazole 1-oxide
5-methyl-6-nitro-2-m-tolyl-2H-benzotriazole 1-oxide
5-methyl-6-nitro-2-o-tolyl-2H-benzotriazole 1-oxide
5-methyl-6-nitro-2-p-tolyl-2H-benzotriazole 1-oxide
6-methyl-4-nitro-2-p-tolyl-2H-benzotriazole 1-oxide
6-methyl-2-phenyl-2H-benzotriazole 1-oxide
4-methyl-2-m-tolyl-2H-benzotriazole 1-oxide
4-methyl-2-o-tolyl-2H-benzotriazole 1-oxide
4-methyl-2-p-tolyl-2H-benzotriazole 1-oxide
6-methyl-2-m-tolyl-2H-benzotriazole 1-oxide
6-methyl-2-o-tolyl-2H-benzotriazole 1-oxide
6-methyl-2-p-tolyl-2H-benzotriazole 1-oxide
2-[1] naphthyl-4,6-dinitro-2H-benzotriazole 1-oxide
2-[2] naphthyl-4,6-dinitro-2H-benzotriazole 1-oxide
2-[1]naphthyl-6-nitro-2H-benzotriazole 1-oxide
2-[2]naphthyl-6-nitro-2H-benzotriazole 1-oxide
2-(3-nitrophenyl)-2H-benzotriazole 1-oxide
6-nitro-2-phenyl-2H-benzotriazole 1-oxide
4-nitro-2-p-tolyl-2H-benzotriazole 1-oxide
6-nitro-2-o-tolyl-2H-benzotriazole 1-oxide
6-nitro-2-p-tolyl-2H-benzotriazole 1-oxide
6-nitro-2-(2,4,5-trimethylphenyl)-2H-benzotriazole 1-oxide 2-phenyl-2H-benzotriazole 1-oxide
2-o-tolyl-2H-benzotriazole 1-oxide
2-p-tolyl-2H-benzotriazole 1-oxide The mediator can preferably furthermore be selected amongst the group consisting of cyclic N-hydroxy compounds having at least one optionally substituted five or six-membered ring which contains the structure mentioned in formula V

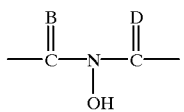

V and their salts, ethers or esters, where

B and D are identical or different and are O, S or $NR^{18}$, $R^{18}$ being hydrogen, hydroxyl, formyl, carbamoyl, sulfono radical, ester or salt of the sulfono radical, sulfamoyl, nitro, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono, phosphonooxy radical, ester or salt of the phosphonooxy radical, it being possible for carbamoyl, sulfamoyl, amino and phenyl radicals to be unsubstituted or mono- or polysubstituted by a radical $R^{19}$ and it being possible for the aryl-$C_1$–$C_5$-alkyl, $C_1$–$C_{12}$-alkoxy, $C_1$–$C_{10}$-carbonyl and carbonyl $C_1$–$C_6$-alkyl radicals to be saturated or unsaturated, branched or unbranched and to be mono- or polysubstituted by a radical $R^{19}$, $R^{19}$ being identical or different and being a hydroxyl, formyl or carboxyl radical, ester or salt of the carboxyl radical, carbamoyl, sulfono or ester or salt of the sulfono radical, sulfamoyl, nitro, amino, phenyl, $C_1$–$C_5$-alkyl or $C_1$–$C_5$-alkoxy radical.

The mediator is preferably selected from the group of the compounds of the general formula VI, VII, VIII or IX,

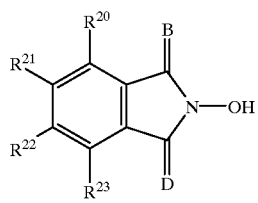

VI

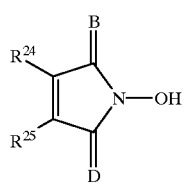

VII

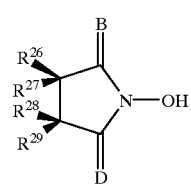

VIII

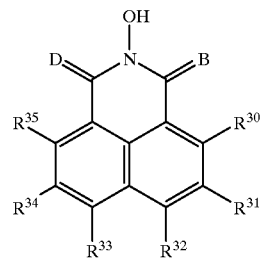

IX where B and D have the meanings which have already been mentioned and the radicals $R^{20}$—$R^{35}$ are identical or different and are a halogen radical, carboxyl radical, salt or ester of a carboxyl radical or have the meanings mentioned for $R^{18}$, where $R^{26}$ and $R^{27}$, or $R^{28}$ and $R^{29}$, respectively, must not simultaneously be a hydroxyl or amino radical, and where, if appropriate, in each case two of the substituents $R^{20}$—$R^{23}$, $R^{24}$—$R^{25}$, $R^{26}$—$R^{29}$, $R^{30}$—$R^{35}$ can be linked to give a ring —E—, —E— having one of the following meanings: (—CH=CH—)$_n$, where n=1 to 3, —CH=CH—CH=N— or

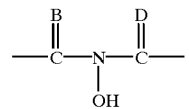

V and where, if appropriate, the radicals $R^{26}$—$R^{29}$ can also be linked to each other by one or more bridging elements —F—, —F— being identical or different and having one of the following meanings: —O—, —S, —CH$_2$—, —CR$^{36}$=CR$^{37}$; $R^{36}$ and $R^{37}$ being identical or different and having the meaning of $R^{20}$.

Especially preferred as mediators are compounds of the general formulae VI, VII, VIII or IX, where B and D are O or S.

Examples of such compounds are N-hydroxyphthalimide and optionally substituted N-hydroxyphthalimide derivatives, N-hydroxymaleimide and optionally substituted N-hydroxymaleimide derivatives, N-hydroxynaphthalimide and optionally substituted N-hydroxynaphthalimide derivatives, N-hydroxysuccinimide and optionally substituted N-hydroxysuccinimide derivatives, preferably those where the radicals $R^{26}$—$R^{29}$ are linked in the form of polycycles.

Particularly preferred as mediator are N-hydroxyphthalimide, 4-amino-N-hydroxyphthalimide and 3-amino-N-hydroxyphthalimide.

Examples of compounds of the formula VI which are suitable as mediator are:
N-hydroxyphthalimide,
4-amino-N-hydroxyphthalimide,
3-amino-N-hydroxyphthalimide,
N-hydroxybenzene-1,2,4-tricarboximide,
N,N'-dihydroxypyromellitic diimide,
N,N'-dihydroxybenzophenone-3,3',4,4'-tetracarboxylic diimide.

Examples of compounds of the formula VII which are suitable as mediator are:
N-hydroxymaleimide,
N-hydroxy-pyridine-2,3-dicarboximide.

Examples of compounds of the formula VIII which are suitable as mediator are:

N-hydroxysuccinimide,
N-hydroxytartarimide,
N-hydroxy-5-norbornene-2,3-dicarboximide,
exo-N-hydroxy-7-oxabicyclo[2.2.1]-hept-5-ene-2,3-dicarboximide,
N-hydroxy-cis-cyclohexane-1,2-dicarboximide,
N-hydroxy-cis-4-cyclohexene-1,2-dicarboximide.

An example of the compound of the formula IX which is suitable as mediator is:
N-hydroxynaphthalimide-sodium salt.

An example of a compound with a six-membered ring containing the structure mentioned in formula V and suitable as mediator is:
N-hydroxyglutarimide.

The compounds which have been mentioned by way of example are also suitable as mediator in the form of their salts or esters.

Also suitable as mediator are compounds selected from the group of the N-aryl-N-hydroxy-amides.

Amongst these, compounds which are preferably employed as mediators are those of the general formula X, XI or XII

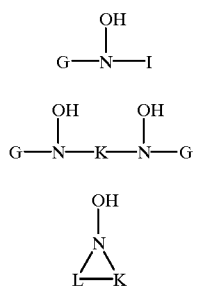

and their salts, ethers or esters, where G is a monovalent homo- or heteroaromatic mono- or binuclear radical and
L is a divalent homo- or heteroaromatic mono- or binuclear radical, and
it being possible for these aromatics to be substituted by one or more identical or different radicals $R^{38}$ selected from the group consisting of halogen, hydroxyl, formyl, cyano, carbamoyl, carboxyl radical, ester or salt of the carboxyl radical, sulfono radical, ester or salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono or phosphonooxy radical, ester or salt of the phosphonooxy radical, and it being possible for carbamoyl, sulfamoyl, amino and phenyl radicals to be unsubstituted or to be mono- or polysubstituted by a radical $R^{39}$ and it being possible for the aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_5$-alkyl radicals to be saturated or unsaturated, branched or unbranched and to be mono- or polysubstituted by a radical $R^{39}$, $R^{39}$ being identical or different and being hydroxyl, formyl, cyano, carboxyl radical, ester or salt of the carboxyl radical, carbamoyl, sulfono, sulfamoyl, nitro, nitroso, amino, phenyl, $C_1$–$C_5$-alkyl, $C_1$–$C_5$-alkoxy or $C_1$–$C_5$-alkylcarbonyl radical and
it being possible for in each case two radicals $R^{38}$ or $R^{39}$ to be linked, in pairs, via a bridge [—$CR^{40}R^{41}$—]$_m$ where m equals 0, 1, 2, 3 or 4 and
$R^{40}$ and $R^{41}$ are identical or different and are a carboxyl radical, ester or salt of the carboxyl radical, phenyl, $C_1$–$C_5$-alkyl, $C_1$–$C_5$-alkoxy or $C_1$–$C_5$-alkylcarbonyl radical and it being possible for one or more nonadjacent groups [—$CR^{40}R^{41}$—] to be replaced by oxygen, sulfur or by an imino radical which is optionally substituted by $C_1$ to $C_5$-alkyl radical and it being possible for two adjacent groups [—$CR^{40}R^{41}$—] to be replaced by a group [—$CR^{40}$=$CR^{41}$—] and I is a monovalent acid radical, present in amide form, of acids selected from the group consisting of carboxylic acid having up to 20 C atoms, carbonic acid, monoester of carbonic acid or of carbamic acid, sulfonic acid, phosphonic acid, phosphoric acid, monoester of phosphoric acid, diester of phosphoric acid and
K is a divalent acid radical, present in amide form, of acids selected from the group consisting of mono- and dicarboxylic acids having up to 20 C atoms, carbonic acid, sulfonic acid, phosphonic acid, phosphoric acid or monoester of phosphoric acid.

Especially preferred as mediators are compounds of the general formula XIII, XIV, XV, XVI or XVII:

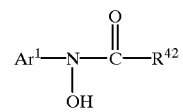

XIII

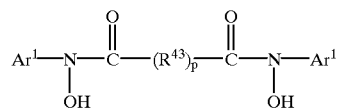

XIV

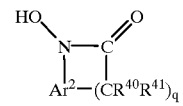

XV

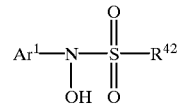

XVI

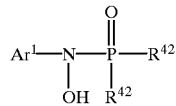

XVII and their salts, ethers or esters, where $Ar^1$ is a monovalent homo- or heteroaromatic mononuclear aryl radical and
$Ar^2$ is a divalent homo- or heteroaromatic mononuclear aryl radical,
each of which can be substituted by one or more identical or different radicals $R^{44}$ selected from the group consisting of hydroxyl, cyano, carboxyl radical, ester or salt of the carboxyl radical, sulfono radical, ester or salt of the sulfono radical, nitro, nitroso, amino, $C_1$–$C_{12}$-alkyl, $C_1$–$C_5$-alkoxy, $C_1$–$C_{10}$-carbonyl or carbonyl-$C_1$–$C_6$-alkyl radical,
it being possible for amino radicals to be unsubstituted or mono- or polysubstituted by a radical $R^{45}$ and it being possible for the $C_1$–$C_{12}$-alkyl, $C_1$–$C_5$-alkoxy, $C_1$–$C_{10}$-carbonyl and carbonyl-$C_1$–$C_6$-alkyl radicals to be saturated or unsaturated, branched or unbranched and to be mono- or polysubstituted by a radical $R^{45}$,
$R^{45}$ being identical or different and being hydroxyl, carboxyl radical, ester or salt of the carboxyl radical, sulfono, nitro, amino, $C_1$–$C_5$-alkyl, $C_1$–$C_5$-alkoxy or $C_1$–$C_5$-alkylcarbonyl radical and
it being possible for in each case two radicals $R^{44}$ to be linked, in pairs, via a bridge [—$CR^{40}R^{41}$—]$_m$ where m equals 0, 1, 2, 3 or 4 and $R^{40}$ and $R^{41}$ have the meanings which have already been mentioned and one or more nonadjacent groups [—$CR^{40}R^{41}$—] can be replaced by oxygen, sulfur or by an imino radical which is optionally substituted by a $C_1$- to $C_5$-alkyl radical, and two adjacent groups [—$CR^{40}R^{41}$—] can be replaced by a group [—$CR^{40}$=$CR^{41}$—], $R^{42}$ is identical or different monovalent radicals selected from the group consisting of hydrogen, phenyl, aryl-$C_1$–$C_5$-alkyl, $C_1$–$C_{12}$-alkyl, $C_1$–$C_5$-alkoxy or $C_1$–$C_{10}$-carbonyl radical, it being possible for phenyl radicals to be unsubstituted or mono- or polysubstituted by a radical $R^{46}$ and it being possible for the aryl-$C_1$–$C_5$-alkyl, $C_1$–$C_{12}$-alkyl, $C_1$–$C_5$-alkoxy and $C_1$–$C_{10}$-carbonyl radicals to be saturated or unsaturated, branched or unbranched and to be mono- or polysubstituted by a radical $R^{46}$, $R^{46}$ being identical or different and being hydroxyl, formyl, cyano, carboxyl radical, ester or salt of the carboxyl radical, carbamoyl, sulfono, sulfamoyl, nitro, nitroso, amino, phenyl, $C_1$–$C_5$-alkyl or $C_1$–$C_5$-alkoxy radical and $R^{43}$ being divalent radicals selected from the group consisting of ortho-, meta-, para-phenylene, aryl-$C_1$–$C_5$-alkyl, $C_1$–$C_{12}$-alkylene or $C_1$–$C_5$-alkylenedioxy radical, it being possible for the phenylene radicals to be unsubstituted or mono- or polysubstituted by a radical $R^{46}$ and it being possible for the aryl-$C_1$–$C_5$-alkyl, $C_1$–$C_{12}$-alkyl or $C_1$–$C_5$-alkoxy radicals to be saturated or unsaturated, branched or unbranched and to be mono- or polysubstituted by a radical $R^{46}$, p being 0 or 1 and q being an integer from 1 to 3.

Preferably, $Ar^1$ is a phenyl radical and $Ar^2$ an ortho-phenylene radical, it being possible for $Ar^1$ to be substituted by up to five and for $Ar^2$ to be substituted by up to four identical or different radicals selected from the group consisting of $C_1$–$C_3$-alkyl, $C_1$–$C_3$-alkylcarbonyl, carboxyl radical, ester or salt of the carboxyl radical, sulfono radical, ester or salt of the sulfono radical, hydroxyl, cyano, nitro, nitroso and amino radical, it being possible for amino radicals to be substituted by two different radicals selected from the group consisting of hydroxyl and $C_1$–$C_3$-alkylcarbonyl.

Preferably, $R^{42}$ is a monovalent radical selected from the group consisting of hydrogen, phenyl, $C_1$–$C_{12}$-alkyl, $C_1$–$C_5$-alkoxy radical, it being possible for the $C_1$–$C_{12}$-alkyl radicals and the $C_1$–$C_5$-alkoxy radicals to be saturated or unsaturated, branched or unbranched.

Preferably, $R^{43}$ is divalent radicals selected from the group consisting of ortho- or para-phenylene, $C_1$–$C_{12}$-alkylene, $C_1$–$C_5$-alkylenedioxy radical, it being possible for the aryl-$C_1$–$C_5$-alkyl, $C_1$–$C_{12}$-alkyl and $C_1$–$C_5$-alkoxy radicals to be saturated or unsaturated, branched or unbranched and to be mono- or polysubstituted by a radical $R^{46}$.

$R^{46}$ is preferably carboxyl radical, ester or salt of the carboxyl radical, carbamoyl, phenyl or $C_1$–$C_3$-alkoxy radical.

Examples of compounds which can be employed as mediators are N-hydroxyacetanilide, N-hydroxypivaloylanilide, N-hydroxyacrylanilide, N-hydroxybenzoylanilide, N-hydroxymethylsulfonylanilide, N-hydroxy-N-phenylmethylcarbamate, N-hydroxy-3-oxo-butyrylanilide, N-hydroxy-4-cyanoacetanilide, N-hydroxy-4-methoxyacetanilide, N-hydroxyphenacetin, N-hydroxy-2,3-dimethylacetanilide, N-hydroxy-2-methylacetanilide, N-hydroxy-4-methylacetanilide, 1-hydroxy-3,4-dihydroquinolin-(1H)-2-one, N,N'-dihydroxy-N,N'-diacetyl-1,3-phenylenediamine, N,N'-dihydroxysuccinanilide, N,N'-dihydroxymaleianilide, N,N'-dihydroxyoxalanilide, N,N'-dihydroxyphosphoranilide, N-acetoxyacetanilide, N-hydroxymethyloxalylanilide, N-hydroxymaleianilide.

Mediators which are preferably used are N-hydroxyacetanilide, N-hydroxyformanilide, N-hydroxy-N-phenylmethylcarbamate, N-hydroxy-2-methylacetanilide, N-hydroxy-4-methylacetanilide, 1-hydroxy-3,4-dihydroquinolin-(1H)-2-one and N-acetoxyacetanilide.

The mediator can furthermore be selected from the group of the N-alkyl-N-hydroxy-amides.

Mediators which are preferably employed are compounds of the general formula (XVIII) or (XIX)

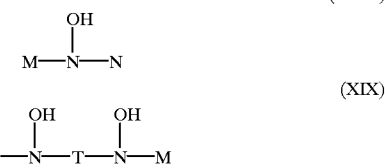

and their salts, ethers or esters, where M is identical or different and is a monovalent linear or branched or cyclic or polycyclic saturated or unsaturated alkyl radical having 1–24 C atoms, and it being possible for this alkyl radical to be substituted by one or more radicals $R^{48}$, which are identical or different and are selected from the group consisting of hydroxyl, mercapto, formyl, carbamoyl, carboxyl, ester or salt of the carboxyl radical, sulfono radical, ester or salt of the sulfono radical, sulfamoyl, nitro, nitroso, amino, hydroxylamino, phenyl, $C_1$–$C_5$-alkoxy, $C_1$–$C_{10}$-carbonyl, phospho, phosphono, phosphonooxy radical, ester or salt of the phosphonooxy radical, and it being possible for carbamoyl, sulfamoyl, amino, hydroxylamino, mercapto and phenyl radicals to be unsubstituted or to be mono- or polysubstituted by a radical $R^{48}$, and it being possible for the $C_1$–$C_5$-alkoxy and $C_1$–$C_{10}$-carbonyl radicals to be saturated or unsaturated, branched or unbranched and to be mono- or polysubstituted by a radical $R^{48}$, $R^{48}$ being identical or different and being hydroxyl, formyl, cyano, carboxyl radical, ester or salt of the carboxyl radical, carbamoyl, sulfono, sulfamoyl, nitro, nitroso, amino, phenyl, benzoyl, $C_1$–$C_5$-alkyl, $C_1$–$C_5$-alkoxy or $C_1$–$C_5$-alkylcarbonyl radical, and it being possible for methylene groups which are not in the α-position to be replaced by oxygen, sulfur or by an optionally monosubstituted imino radical, and where N is a monovalent acid radical, present in amide form, of acids selected from the group consisting of aliphatic or mono- or binuclear aromatic or mono- or binuclear hetero-aromatic carboxylic acids having up to 20 C atoms, carbonic acid, monoester of carbonic acid or of carbamic acid, sulfonic acid, phosphonic acid, phosphoric acid, monoester of phosphoric acid, diester of phosphoric acid, and T is a divalent acid radical, present in amide form, of acids selected from the group consisting of aliphatic, mono- or binuclear aromatic or mono- or binuclear hetero-aromatic dicarboxylic acids having up to 20 C atoms, carbonic acid, sulfonic acid, phosphonic acid, phosphoric acid, monoester of phosphoric acid, and it being possible for alkyl radicals of the aliphatic acids N and T, present in amide form, to be linear or branched and/or to be saturated or unsaturated in the cycle and/or polycycle and to contain 0–24 carbon atoms and to be unsubstituted or to be mono- or polysubstituted by the radical $R^{47}$ and it being possible for aryl and heteroaryl radicals of the aromatic or heteroaromatic acids N and T, present in amide form, to be substituted by one or more radicals $R^{49}$ which are identical or different and are selected from the group consisting of hydroxyl, mercapto, formyl, cyano, carbamoyl, carboxyl, ester or salt of the carboxyl radical, sulfono radical, ester or salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1$–$C_{10}$-carbonyl, phospho, phosphono, phosphonooxy radical, ester or salt of the phosphonooxy radical and it being possible for carbamoyl, sulfamoyl, amino, mercapto and phenyl radicals to be unsubstituted or mono- or polysubstituted by the radical $R^{48}$ and it being possible for the aryl-$C_1$–$C_5$-alkyl, $C_1$–$C_{12}$-alkyl-$C_1$–$C_5$-alkoxy and $C_1$–$C_{10}$-carbonyl radicals to be saturated or unsaturated, branched or unbranched and to be mono- or polysubstituted by the radical $R^{48}$.

Especially preferred as mediators are compounds of the general formula (XX, XXI, XXII or XXIII):

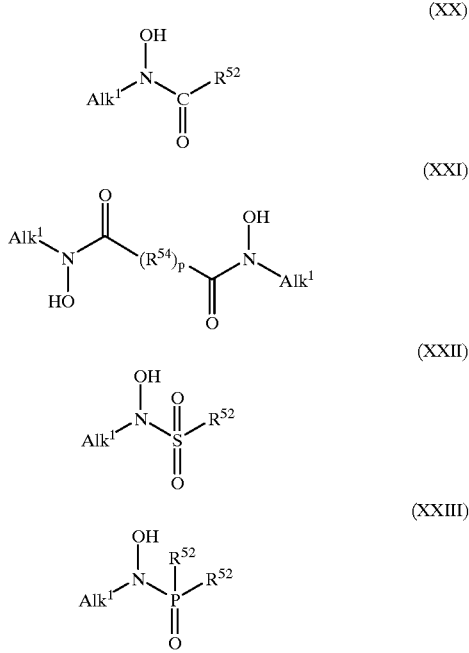

and their salts, ethers or esters, where $Alk^1$ is identical or different and is a monovalent linear or branched or cyclic or polycyclic saturated or unsaturated alkyl radical having 1–10 C atoms, it being possible for this alkyl radical to be substituted by one or more radicals $R^{50}$ which are identical or different and are selected from the group consisting of hydroxyl, formyl, carbamoyl, carboxyl, ester or salt of the carboxyl radical, sulfono radical, ester or salt of the sulfono radical, sulfamoyl, nitro, nitroso, amino, hydroxylamino, phenyl, $C_1$–$C_5$-alkoxy or $C_1$–$C_5$-carbonyl radicals and it being possible for carbamoyl, sulfamoyl, amino, hydroxylamino and phenyl radicals to be unsubstituted or to be mono- or polysubstituted by a radical $R^{51}$ and it being possible for the $C_1$–$C_5$-alkoxy and $C_1$–$C_{10}$-carbonyl radicals to be saturated or unsaturated, branched or unbranched and to be mono- or polysubstituted by a radical $R^{51}$, $R^{51}$ being identical or different and being hydroxyl, formyl, cyano, carboxyl radical, ester or salt of the carboxyl radical, carbamoyl, sulfono, sulfamoyl, nitro, amino, phenyl, benzoyl, $C_1$–$C_5$-alkyl, $C_1$–$C_5$-alkoxy or $C_1$–$C_5$-alkylcarbonyl radical and it being possible for methylene groups which are not in the a-position to be replaced by oxygen, sulfur or by an optionally monosubstituted imino radical and $R^{52}$ being identical or different monovalent radicals selected from the group consisting of hydrogen, phenyl, pyridyl, furyl, pyrrolyl, thienyl, aryl-$C_1$–$C_5$-alkyl, $C_1$–$C_{12}$-alkyl, $C_1$–$C_{10}$-alkoxy or $C_1$–$C_{10}$-carbonyl radical, it being possible for phenyl, pyridyl, furyl, pyrrolyl and thienyl radicals to be unsubstituted or to be mono- or polysubstituted by a radical $R^7$ and it being possible for the aryl-$C_1$–$C_5$-alkyl, $C_1$–$C_{12}$-alkyl, $C_1$–$C_5$-alkoxy and $C_1$–$C_{10}$-carbonyl radicals to be saturated or unsaturated, branched or unbranched and to be mono- or polysubstituted by a radical $R^{53}$ and $R^{53}$ is identical or different and is hydroxyl, formyl, carboxyl radical, ester or salt of the carboxyl radical, carbamoyl, sulfono, sulfamoyl, nitro, amino, phenyl, $C_1$–$C_5$-alkyl or $C_1$–$C_5$-alkoxy radical and $R^{54}$ is divalent radicals selected from the group consisting of phenylene, pyridylene, thienylene, furylene, pyrrolylene, aryl-$C_1$–$C_5$-alkyl, $C_1$–$C_{12}$-alkylene or $C_1$–$C_5$-alkylenedioxy radical, it being possible for phenylene, pyridylene, thienylene, furylene and pyrrolylene to be unsubstituted or to be mono- or polysubstituted by a radical $R^{53}$ and it being possible for the aryl-$C_1$–$C_5$-alkyl, $C_1$–$C_{12}$-alkyl and $C_1$–$C_5$-alkoxy radicals to be saturated or unsaturated, branched or unbranched and to be mono- or polysubstituted by a radical $R^{53}$, p being 0 or 1.

Very especially preferred as mediators are compounds of the general formulae (XX–XXIII), where $Alk^1$ is identical or different and is a monovalent linear or branched or cyclic saturated or unsaturated alkyl radical having 1–10 C atoms, it being possible for this alkyl radical to be substituted by one or more radicals $R^{50}$ which are identical or different and are selected from the group consisting of hydroxyl, carbamoyl, carboxyl, ester or salt of the carboxyl radical, sulfono radical, ester or salt of the sulfono radical, sulfamoyl, amino, phenyl, $C_1$–$C_5$-alkoxy or $C_1$–$C_5$-carbonyl radicals and it being possible for carbamoyl, sulfamoyl, amino and phenyl radicals to be unsubstituted or to be mono- or polysubstituted by a radical $R^{51}$ and it being possible for the $C_1$–$C_5$-alkoxy and $C_1$–$C_{10}$-carbonyl radicals to be saturated or unsaturated, branched or unbranched and to be mono- or polysubstituted by a radical $R^{51}$, $R^{51}$ being identical or different and being hydroxyl, carboxyl radical, ester or salt of the carboxyl radical, carbamoyl, sulfono, sulfamoyl, nitro, amino, phenyl, benzoyl, $C_1$–$C_5$-alkyl, $C_1$–$C_5$-alkoxy or $C_1$–$C_5$-alkylcarbonyl radical and $R^{52}$ being identical or different monovalent radicals selected from the group consisting of hydrogen, phenyl, furyl, aryl-$C_1$–$C_5$-alkyl, $C_1$–$C_{12}$-alkyl, $C_1$–$C_{10}$-alkoxy or $C_1$–$C_{10}$-carbonyl radical, it being possible for phenyl and furyl radicals to be unsubstituted or to be mono- or polysubstituted by a radical $R^{53}$ and it being possible for the aryl-$C_1$–$C_5$-alkyl, $C_1$–$C_{12}$-alkyl, $C_1$–$C_5$-alkoxy and $C_1$–$C_{10}$-carbonyl radicals to be saturated or unsaturated, branched or unbranched and to be mono- or polysubstituted by a radical $R^{53}$, $R^{53}$ being identical or different and being a carboxyl radical, ester or salt of the carboxyl radical, carbamoyl, phenyl, $C_1$–$C_5$-alkyl or $C_1$–$C_5$-alkoxy radical and $R^{54}$ is a divalent radical selected from the group consisting of phenylene, furylene, $C_1$–$C_{12}$-alkylene and $C_1$–$C_5$-alkylenedioxy radical, it being possible for phenylene and furanylene to be unsubstituted or to be mono- or polysubstituted by a radical $R^{53}$ and it being possible for the aryl-$C_1$–$C_5$-alkyl, $C_1$–$C_{12}$-alkyl and $C_1$–$C_5$-alkoxy radicals to be saturated or unsaturated, branched or unbranched and to be mono- or polysubstituted by a radical $R^{53}$, p being 0 or 1.

Examples of compounds which can be employed as mediators are
N-hydroxy-N-methylbenzamide, N-hydroxy-N-methylbenzenesulfonamide, N-hydroxy-N-methyl-p-toluenesulfonamide, N-hydroxy-N-methylfuran-2-carboxamide, N-hydroxy-N-methylthiophene-2-carboxamide, N,N'-dihydroxy-N,N'-dimethylphthalamide, N,N'-dihydroxy-N,N'-dimethylisophthalamide, N,N'-dihydroxy-N,N'-dimethylterephthalamide, N,N'-dihydroxy-N,N'-dimethylbenzene-1,3-disulfonamide, N,N'-dihydroxy-N,N'-dimethylfuran-3,4-dicarboxamide, N-hydroxy-N-tert-butylbenzamide, N-hydroxy-N-tert-butylbenzenesulfonamide, N-hydroxy-N-tert-butyl-p-toluenesulfonamide,
N-hydroxy-N-tert-butylfuran-2-carboxamide, N-hydroxy-N-tert-butylthiophene-2-carboxamide, N,N'-dihydroxy-N,N'-di-tert-butylphthalamide, N,N'-dihydroxy-N,N'-di-tert-butylisophthalamide, N,N'-dihydroxy-N,N'-di-tert-butylterephthalamide, N,N'-dihydroxy-N,N'-di-tert-butylbenzene-1,3-disulfonamide, N,N'-dihydroxy-N,N'-di-tert-butylfuran-3,4-dicarboxamide, N-hydroxy-N-cyclohexylbenzamide, N-hydroxy-N-cyclohexylbenzenesulfonamide,
N-hydroxy-N-cyclohexyl-p-toluenesulfonamide, N-hydroxy-N-cyclohexylfuran-2-carboxamide, N-hydroxy-N-cyclohexylthiophene-2-carboxamide, N,N'-dihydroxy-N,N'-dicyclohexylphthalamide, N,N'-dihydroxy-N,N'-dicyclohexylisophthalamide, N,N'-dihydroxy-N,N'-dicyclohexylterephthalamide, N,N'-dihydroxy-N,N'-dicyclohexylbenzene-1,3-disulfonamide, N,N'-dihydroxy-N,N'-dicyclohexylfuran-3,4-dicarboxamide, N-hydroxy-N-isopropylbenzamide, N-hydroxy-N-isopropylbenzenesulfonamide, N-hydroxy-N-isopropyl-p-toluenesulfonamide, N-hydroxy-N-isopropylfuran-2-carboxamide, N-hydroxy-N-isopropylthiophene-2-carboxamide, N,N'-dihydroxy-N,N'-diisopropylphthalamide, N,N'-dihydroxy-N,N'-diisopropylisophthalamide, N,N'-dihydroxy-N,N'-diisopropylterephthalamide, N,N'-dihydroxy-N,N'-diisopropylbenzene-1,3-disulfonamide, N,N'-dihydroxy-N,N'-diisopropylfuran-3,4-dicarboxamide, N-hydroxy-N-methylacetamide, N-hydroxy-N-tert-butylacetamide, N-hydroxy-N-isopropylacetamide, N-hydroxy-N-cyclohexylacetamide, N-hydroxy-N-methylpivalamide, N-hydroxy-N-isopropyl-pivalamide, N-hydroxy-N-methylacrylamide, N-hydroxy-N-tert-butylacrylamide, N-hydroxy-N-isopropyl-acrylamide, N-hydroxy-N-cyclohexylacrylamide, N-hydroxy-N-methylmethanesulfonamide, N-hydroxy-N-isopropylmethane-sulfonamide, N-hydroxy-N-isopropylmethylcarbamate, N-hydroxy-N-methyl-3-oxobutyramide, N,N'-dihydroxy-N,N'-dibenzoylethylenediamine, N,N'-dihydroxy-N,N'-dimethylsuccinamide,
N,N'-dihydroxy-N,N'-di-tert-butylmaleamide, N-hydroxy-N-tert-butylmaleamide, N,N'-dihydroxy-N,N'-di-tert-butyloxalamide, N,N'-dihydroxy-N,N -di-tert-butylphosphoramide.

Compounds which are preferably selected as mediators are from the group consisting of N-hydroxy-N-methylbenzamide, N-hydroxy-N-methylbenzenesulfonamide, N-hydroxy-N-methyl-p-toluenesulfonamide, N-hydroxy-N-methylfuran-2-carboxamide, N,N'-dihydroxy-N,N'-dimethylphthalamide, N,N'-dihydroxy-N,N'-dimethylterephthalamide, N,N'-dihydroxy-N,N'-dimethylbenzene-1,3-disulfonamide, N-hydroxy-N-tert-butylbenzamide, N-hydroxy-N-tert-butylbenzenesulfonamide, N-hydroxy-N-tert-butyl-p-toluenesulfonamide, N-hydroxy-N-tert-butylfuran-2-carboxamide, N,N'-dihydroxy-N,N'-di-tert-butylterephthalamide, N-hydroxy-N-isopropylbenzamide, N-hydroxy-N-isopropyl-p-toluenesulfonamide, N-hydroxy-N-isopropylfuran-2-carboxamide, N,N'-dihydroxy-N,N'-diisopropylterephthalamide, N,N'-dihydroxy-N,N'-diisopropylbenzene-1,3-disulfonamide, N-hydroxy-N-methylacetamide, N-hydroxy-N-tert-butylacetamide, N-hydroxy-N-isopropylacetamide, N-hydroxy-N-cyclohexylacetamide, N-hydroxy-N-methylpivalamide, N-hydroxy-N-tert-butylacrylamide, N-hydroxy-N-isopropylacrylamide, N-hydroxy-N-methyl-3-oxobutyramide, N,N'-dihydroxy-N,N'-dibenzoylethylenediamine,
N,N'-dihydroxy-N,N'-di-tert-butylmaleamide, N-hydroxy-N-tert-butylmaleamide, N,N'-dihydroxy-N,N'-di-tert-butyloxalamide.

The mediator can furthermore be selected from the group of the oximes of the general formula XXIV or XXV

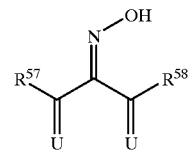

XXIV

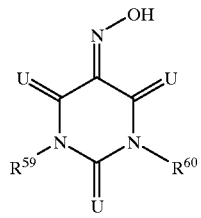

XXV and their salts, ethers or esters, where U is identical or different and is O, S or $NR^{55}$, $R^{55}$ being hydrogen, hydroxyl, formyl, carbamoyl, sulfono radical, ester or salt of the sulfono radical, sulfamoyl, nitro, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono or phosphonooxy radical, ester or salt of the phosphonooxy radical, it being possible for carbamoyl, sulfamoyl, amino and phenyl radicals to be unsubstituted or to be mono- or polysubstituted by a radical $R^{56}$ and it being possible for the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals to be saturated or unsaturated, branched or unbranched and to be mono- or polysubstituted by a radical $R^{56}$, $R^{56}$ being identical or different and being hydroxyl, formyl, carboxyl radical, ester or salt of the carboxyl radical, carbamoyl, sulfono, ester or salt of the sulfono radical, sulfamoyl, nitro, amino, phenyl, $C_1$–$C_5$-alkyl or $C_1$–$C_5$-alkoxy radical and the radicals $R^{57}$ and $R^{58}$ being identical or different and being halogen, carboxyl radical, ester or salt of the carboxyl radical, or having the meanings mentioned for $R^{55}$, or being linked to a ring $[—CR^{61}R^{62}]_n$ where n equals 2, 3 or 4 and $R^{59}$ and $R^{60}$ having the meanings mentioned for $R^{55}$ and $R^{61}$ and $R^{62}$ being identical or different and being halogen, carboxyl radical, ester or salt of the carboxyl radical, or having the meanings mentioned for $R^{55}$.

Especially preferred as mediators are compounds of the general formula XXIV where U is O or S and the remaining radicals have the meanings mentioned above. An example of such a compound is dimethyl 2-hydroxyiminomalonate.

Furthermore especially preferred as mediators are isonitroso derivatives of cyclic ureides of the general formula XXV. Examples of such compounds are 1-methyl-violuric acid, 1,3-dimethylvioluric acid, thiovioluric acid, alloxane 4,5-dioxime.

Particularly preferred as mediator is alloxane 5-oxime hydrate (violuric acid) and/or its esters, ethers or salts.

The mediator can furthermore be selected from the group of the vicinally nitroso-substituted aromatic alcohols of the general formula XXVI or XXVII

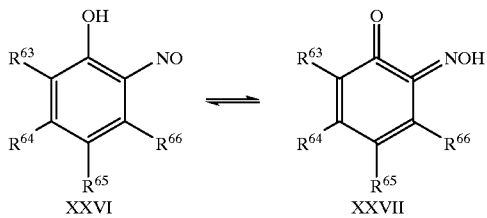

and their salts, ethers or esters, where
$R^{63}$, $R^{64}$, $R^{65}$ and $R^{66}$ are identical or different and are hydrogen, halogen, hydroxyl, formyl, carbamoyl, carboxyl radical, ester or salt of the carboxyl radical, sulfono radical, ester or salt of the sulfono radical, sulfamoyl, nitro, nitroso, cyano, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono or phosphonooxy radical, ester or salt of the phosphonooxy radical,
it being possible for carbamoyl, sulfamoyl, amino and phenyl radicals to be unsubstituted or to be mono- or polysubstituted by a radical $R^{67}$ and it being possible for the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals to be saturated or unsaturated, branched or unbranched and to be mono- or polysubstituted by a radical $R^{67}$,
$R^{67}$ being identical or different and being hydroxyl, formyl, carboxyl radical, ester or salt of the carboxyl radical, carbamoyl, sulfono, sulfamoyl, nitro, nitroso, amino, phenyl, $C_1$–$C_5$-alkyl or $C_1$–$C_5$-alkoxy radical, or it being possible for the radicals $R^{63}$—$R^{66}$, in pairs, to be linked to give a ring $[CR^{68}R^{69}—]_m$ where m is an integer and denotes a value of 1 to 4, or linked to give a ring $[CR^{70}=CR^{71}—]_n$, where n is an integer and denotes a value of 1 to 3, and $R^{68}$, $R^{69}$, $R^{70}$ and $R^{71}$ being identical or different and having the meanings mentioned for $R^{63}$ to $R^{66}$.

Aromatic alcohols are preferably to be understood as meaning phenols or higher-condensed phenol derivatives.

Preferred as mediators are compounds of the general formula XXVI or XXVII whose synthesis can be based on the nitrosization of substituted phenols. Examples of such compounds are 2-nitrosophenol, 3-methyl-6-nitrosophenol, 2-methyl-6-nitrosophenol, 4-methyl-6-nitrosophenol, 3-ethyl-6-nitrosophenol, 2-ethyl-6-nitrosophenol, 4-ethyl-6-nitrosophenol, 4-isopropyl-6-nitrosophenol, 4-tert-butyl-6-nitrosophenol, 2-phenyl-6-nitrosophenol, 2-benzyl-6-nitrosophenol, 4-benzyl-6-nitrosophenol, 2-hydroxy-3-nitrosobenzyl alcohol, 2-hydroxy-3-nitrosobenzoic acid, 4-hydroxy-3-nitrosobenzoic acid, 2-methoxy-6-nitrosophenol, 3,4-dimethyl-6-nitrosophenol, 2,4-dimethyl-6-nitrosophenol, 3,5-dimethyl-6-nitrosophenol, 2,5-dimethyl-6-nitrosophenol, 2-nitrosoresorcin, 4-nitrosoresorcin, 2-nitrosoorcin, 2-nitrosophloroglucine and 4-nitrosopyrogallol, 4-nitroso-3-hydroxyaniline, 4-nitro-2-nitrosophenol.

Furthermore preferred as mediators are o-nitroso derivatives of higher-condensed aromatic alcohols. Examples of such compounds are 2-nitroso-1-naphthol, 1-methyl-3-nitroso-2-naphthol and 9-hydroxy-10-nitrosophenanthrene.

Especially preferred as mediators are 1-nitroso-2-naphthol, 1-nitroso-2-naphthol-3,6-disulfonic acid, 2-nitroso-1-naphthol-4-sulfonic acid, 2,4-dinitroso-1,3-dihydroxybenzene, and esters, ethers or salts of the compounds mentioned.

The mediator can furthermore be selected from the group consisting of hydroxypyridines, aminopyridines, hydroxyquinolines, aminoquinolines, hydroxyisoquinolines, aminoisoquinolines, with the nitroso or mercapto substituents which are in the ortho- or para-positions relative to the hydroxyl or amino groups, tautomers of the compounds mentioned, and their salts, ethers and esters.

Preferred as mediators are compounds of the general formula (XXVIII), (XXIX) or (XXX)

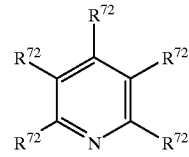
(XXVIII)

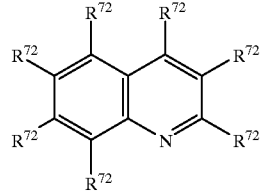
(XXIX)

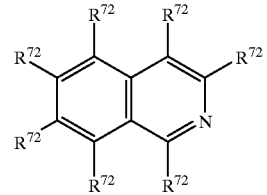
(XXX)

and tautomers, salts, ethers or esters of the compounds mentioned, where, in formulae XXVIII, XXIX and XX, two radicals $R^{72}$ which are in the ortho- or para-position relative to each other are the hydroxyl and nitroso radical or hydroxyl and mercapto radical or nitroso radical and amino radical
and the remaining radicals $R^{72}$ are identical or different are selected from the group consisting of hydrogen, halogen, hydroxyl, mercapto, formyl, cyano, carbamoyl, carboxyl radical, ester and salt of the carboxyl radical, sulfono radical, ester and salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono and phosphonooxy radical, ester and salt of the phosphonooxy radical, and it being possible for carbamoyl, sulfamoyl, amino, mercapto and phenyl radicals to be unsubstituted or to be mono- or polysubstituted by a radical $R^{73}$, and it being possible for the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals to be saturated or unsaturated, branched or unbranched and to be mono- or polysubstituted by a radical $R^{73}$, $R^{73}$ being identical or different and being hydroxyl, formyl, cyano, carboxyl radical, ester or salt of the carboxyl radical, carbamoyl, sulfono, sulfamoyl, nitro, nitroso, amino, phenyl, $C_1$–$C_5$-alkyl, $C_1$–$C_5$-alkoxy radical or $C_1$–$C_5$-alkylcarbonyl radical and it being possible for in each case two radicals $R^{72}$ or two radicals $R^{73}$ or $R^{72}$ and $R^{73}$, in pairs, to be linked via a bridge [—$CR^{74}R^{75}$—]$_m$ where m equals 1, 2, 3 or 4 and $R^3$ and $R^4$ are identical or different and are a carboxyl radical, ester or salt of the carboxyl radical, phenyl, $C_1$–$C_5$-alkyl, $C_1$–$C_5$-alkoxy radical or $C_1$–$C_5$-alkylcarbonyl radical and it being possible for one or more nonadjacent groups [—$CR^{74}R^{75}$—] to be replaced by oxygen, sulfur or by an imino radical which is optionally substituted by $C_1$–$C_5$-alkyl, and it being possible for two adjacent groups [—$CR^{74}R^{75}$—] to be replaced by a group [—$CR^{74}$=$R^{75}$—].

Especially preferred as mediators are compounds of the general formula (XXVIII) or (XXIX) and their tautomers, salts, ethers or esters, where, in formulae (XXVIII) and (XXIX) especially preferred meanings of two radicals $R^{72}$ in the ortho-position relative to each other are the hydroxyl and nitroso radical or hydroxyl and mercapto radical or nitroso radical and amino radical and the remaining radicals $R^{72}$ are identical or different and are selected from the group consisting of hydrogen, hydroxyl, mercapto, formyl, carbamoyl, carboxyl radical, ester and salt of the carboxyl radical, sulfono radical, ester and salt of the sulfono radical, sulfamoyl, nitro, nitroso, amino, phenyl, aryl-$C_1$–$C_5$-alkyl, $C_1$–$C_5$-alkyl, $C_1$–$C_5$-alkoxy, $C_1$–$C_5$-carbonyl, carbonyl-$C_1$–$C_6$-alkyl, phospho, phosphono and phosphonooxy radical, ester and salt of the phosphonooxy radical, it being possible for carbamoyl, sulfamoyl, amino, mercapto and phenyl radicals to be unsubstituted or to be mono- or polysubstituted by a radical $R^{73}$ and it being possible for the aryl-$C_1$–$C_5$-alkyl, $C_1$–$C_5$-alkyl, $C_1$–$C_5$-alkoxy, $C_1$–$C_5$-carbonyl and carbonyl-$C_1$–$C_6$-alkyl radicals to be saturated or unsaturated, branched or unbranched and to be mono- or polysubstituted by a radical $R^{73}$, $R^{73}$ having the meanings which have already been mentioned and it being possible for in each case two radicals $R^{73}$, in pairs, to be linked via a bridge [—$CR^{74}R^{75}$—]$_m$ where m equals 2, 3 or 4 and $R^{74}$ and $R^{75}$ having the meanings which have already been mentioned and it being possible for one or more nonadjacent groups [—$CR^{74}R^{75}$—] to be replaced by oxygen or by an imino radical which is optionally substituted by $C_1$–$C_5$-alkyl.

Examples of compounds which can be employed as mediators are 2,6-dihydroxy-3-nitrosopyridine, 2,3-dihydroxy-4-nitrosopyridine,
2,6-dihydroxy-3-nitrosopyridine-4-carboxylic acid, 2,4-dihydroxy-3-nitrosopyridine, 3-hydroxy-2-mercaptopyridine, 2-hydroxy-3-mercaptopyridine, 2,6-diamino-3-nitrosopyridine, 2,6-diamino-3-nitrosopyridine-4-carboxylic acid,
2-hydroxy-3-nitrosopyridine, 3-hydroxy-2-nitrosopyridine, 2-mercapto-3-nitrosopyridine, 3-mercapto-2-nitrosopyridine, 2-amino-3-nitrosopyridine, 3-amino-2-nitrosopyridine, 2,4-dihydroxy-3-nitrosoquinoline, 8-hydroxy-5-nitrosoquinoline,
2,3-dihydroxy-4-nitrosoquinoline, 3-hydroxy-4-nitrosoisoquinoline,
4-hydroxy-3-nitrosoisoquinoline, 8-hydroxy-5-nitrosoisoquinoline and tautomers of these compounds.

Preferred as mediators are 2,6-dihydroxy-3-nitrosopyridine, 2,6-diamino-3-nitrosopyridine, 2,6-dihydroxy-3-nitrosopyridine-4-carboxylic acid, 2,4-dihydroxy-3-nitrosopyridine, 2-hydroxy-3-mercaptopyridine, 2-mercapto-3-pyridinol, 2,4-dihydroxy-3-nitrosoquinoline, 8-hydroxy-5-nitrosoquinoline, 2,3-dihydroxy-4-nitrosoquinoline and tautomers of these compounds.

The mediator can furthermore be selected from the group of the stable nitroxyl radicals (nitroxides), i.e. these free radicals can be obtained, characterized and stored in pure form.

Mediators which are preferably employed in this case are compounds of the general formula (XXXI), (XXXII) or (XXXIII)

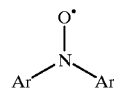
(XXXI)

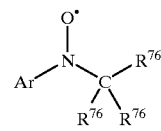
(XXXII)

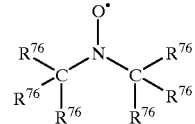
(XXXIII)

where
Ar is a monovalent homo- or heteroaromatic mono- or binuclear radical, and
it being possible for this aromatic radical to be substituted by one or more, identical or different radicals $R^{77}$ selected from the group consisting of halogen, formyl, cyano, carbamoyl, carboxyl, ester or salt of the carboxyl radical, sulfono radical, ester or salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono and phosphonooxy radical, ester or salt of the phosphonooxy radical, and
it being possible for phenyl, carbamoyl and sulfamoyl radicals to be unsubstituted or mono- or polysubstituted by a radical $R^{78}$, it being possible for the amino radical to be mono- or disubstituted by $R^{78}$ and it being possible for the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals to be saturated or unsaturated, branched or unbranched and to be mono- or polysubstituted by a radical $R^{78}$,
it being possible for $R^{78}$ to be present once or more than once, $R^{78}$ being identical or different and being hydroxyl, formyl, cyano, carboxyl radical, ester or salt of the carboxyl radical, carbamoyl, sulfono, sulfamoyl, nitro, nitroso, amino, phenyl, $C_1$–$C_5$-alkyl, $C_1$–$C_5$-alkoxy or $C_1$–$C_5$-alkylcarbonyl radical and
$R^{76}$ is identical or different and is halogen, hydroxyl, mercapto, formyl, cyano, carbamoyl, carboxyl radical, ester or salt of the carboxyl radical, sulfono radical, ester or salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono, phosphonooxy radical, ester or salt of the phosphonooxy radical and, in the case of bicyclic stable nitroxyl radicals (structure XXXIII), $R^{76}$ can also be hydrogen, and it being possible for carbamoyl, sulfamoyl, amino, mercapto and phenyl radicals to be unsubstituted or to be mono- or polysubstituted by a radical $R^{79}$ and it being possible for the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals to be saturated or unsaturated, branched or unbranched and to be mono- or polysubstituted by a radical $R^{79}$, $R^{79}$ being identical or different and being hydroxyl, formyl, cyano, carboxyl radical, ester or salt of the carboxyl radical, carbamoyl, sulfono, sulfamoyl, nitro, nitroso, amino, phenyl, $C_1$–$C_5$-alkyl, $C_1$–$C_5$-alkoxy radical or $C_1$–$C_5$-alkylcarbonyl radical, and it being possible for in each case two radicals $R^{78}$ or $R^{79}$, in pairs, to be linked via a bridge [—$CR^{80}R^{81}$—]$_m$ where m equals 0, 1, 2, 3 or 4, and $R^{80}$ and $R^{81}$ being identical or different and being halogen, carboxyl radical, ester or salt of the carboxyl radical, carbamoyl, sulfamoyl, phenyl, benzoyl, $C_1$–$C_5$-alkyl, $C_1$–$C_5$-alkoxy radical or $C_1$–$C_5$-alkylcarbonyl radical, and it being possible for one or more nonadjacent groups [—$CR^{80}R^{81}$—] to be replaced by oxygen, sulfur or by an imino radical which is optionally substituted by $C_1$–$C_5$-alkyl, and it being possible for two adjacent groups [—$CR^{80}R^{81}$—] to be replaced by a group [—$CR^{80}$=$CR^{81}$—], [—$CR^{80}$=N—] or [—$CR^{80}$=N(O)—].

Especially preferred as mediators are nitroxyl radicals of the general formulae (XXXIV) and (XXXV),

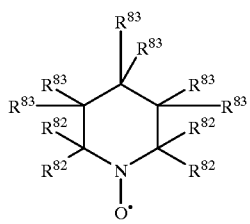

(XXXIV)

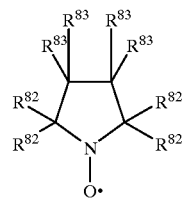

(XXXV)

where $R^{82}$ is identical or different and is phenyl, aryl-$C_1$–$C_5$-alkyl, $C_1$–$C_{12}$-alkyl, $C_1$–$C_5$-alkoxy, $C_1$–$C_{10}$-carbonyl or carbonyl-$C_1$–$C_5$-alkyl, it being possible for phenyl radicals to be unsubstituted or to be mono- or polysubstituted by a radical $R^{84}$ and it being possible for the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals to be saturated or unsaturated, branched or unbranched and to be mono- or polysubstituted by a radical it being possible for $R^{84}$ to be present once or more than once, $R^{84}$ being identical or different and being hydroxyl, formyl, carboxyl radical, ester or salt of the carboxyl radical, carbamoyl, sulfono, sulfamoyl, nitro, nitroso, amino, phenyl, benzoyl, $C_1$–$C_5$-alkyl, $C_1$–$C_5$-alkoxy radical or $C_1$–$C_5$-alkylcarbonyl radical and $R^{83}$ is identical or different and is hydrogen, hydroxyl, mercapto, formyl, cyano, carbamoyl, carboxyl radical, ester or salt of the carboxyl radical, sulfono radical, ester or salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono or phosphonooxy radical, ester or salt of the phosphonooxy radical, it being possible for carbamoyl, sulfamoyl, amino, mercapto and phenyl radicals to be unsubstituted or to be mono- or polysubstituted by a radical $R^{78}$ and it being possible for the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals to be saturated or unsaturated, branched or unbranched and to be mono- or polysubstituted by a radical $R^{78}$ and it being possible for a [—$CR^{83}R^{83}$—] group to be replaced by oxygen, an imino radical which is optionally substituted by $C_1$–$C_5$-alkyl, a (hydroxy)imino radical, a carbonyl function or by a vinylidene function which is optionally mono- or disubstituted by $R^{76}$ and it being possible for two adjacent groups [—$CR^{83}R^{83}$—] to be replaced by a group [—$CR^{83}$=$CR^{83}$—] or [—$CR^{83}$=N—] or [—$CR^{83}$=N(O)—].

Examples of compounds which can be employed as mediators are 2,2,6,6-tetramethyl-1-piperidinyloxy (TEMPO), 4-hydroxy-2,2,6,6-tetramethyl-1-piperidinyloxy, 4-oxo-2,2,6,6-tetramethyl-1-piperidinyloxy, 4-acetamido-2,2,6,6-tetramethyl-1-piperidinyloxy, 4-(ethoxyfluorophosphinyloxy)-2,2,6,6-tetramethyl-1-piperidinyloxy, 4-(isothiocyanato)-2,2,6,6-tetramethyl-1-piperidinyloxy, 4-maleimido-2,2,6,6-tetramethyl-1-piperidinyloxy, 4-(4-nitrobenzoyloxy)-2,2,6,6-tetramethyl-1-piperidinyloxy, 4-(phosphonooxy)-2,2,6,6-tetramethyl-1-piperidinyloxy, 4-cyano-2,2,6,6-tetramethyl-1-piperidinyloxy, 3-carbamoyl-2,2,5,5-tetramethyl-3-pyrroline-1-oxyl, 4-phenyl-2,2,5,5-tetramethyl-3-imidazolin-1-yloxy-3-oxide, 4-carbamoyl-2,2,5,5-tetramethyl-3-imidazolin-1-yloxy-3-oxide, 4-phenacetylidene-2,2,5,5-tetramethylimidazolin-1-yloxy, 3-(aminomethyl)-2,2,5,5-tetramethyl-N-pyrrolidinyloxy, 3-carbamoyl-2,2,5,5-tetramethyl-N-pyrrolidinyloxy, 3-carboxy-2,2,5,5-tetramethyl-N-pyrrolidinyloxy, 3-cyano-2,2,5,5-tetramethyl-N-pyrrolidinyloxy, 3-maleimido-2,2,5,5-tetramethyl-N-pyrrolidinyloxy, 3-(4-nitrophenoxycarbonyl)-2,2,5,5-tetramethyl-N-pyrrolidinyloxy.

Preferred mediators are 2,2,6,6-tetramethyl-1-piperidinyloxy (TEMPO), 4-hydroxy-2,2,6,6-tetramethyl-1-piperidinyloxy, 4-oxo-2,2,6,6-tetramethyl-1-piperidinyloxy, 4-acetamido-2,2,6,6-tetramethyl-1-piperidinyloxy, 4-(isothiocyanato)-2,2,6,6-tetramethyl-1-piperidinyloxy, 4-maleimido-2,2,6,6-tetramethyl-1-piperidinyloxy, 4-(4-nitrobenzoyloxy)-2,2,6,6-tetramethyl-1-piperidinyloxy, 4-(phosphonooxy)-2,2,6,6-tetramethyl-1-piperidinyloxy, 4-cyano-2,2,6,6-tetramethyl-1-piperidinyloxy, 3-carbamoyl-2,2,5,5-tetramethyl-1-pyrrolinidinyloxy, 4-phenyl-2,2,5–5-tetramethyl-3-imidazolin-1-yloxy-3-oxide, 4-carbamoyl-2,2,5–5-tetramethyl-3-imidazolin-1-yloxy-3-oxide, 4-phenacetylidene-2,2,5,5-tetramethyl-1-imidazolidinyloxy.

Particularly preferred as mediators are 2,2,6,6-tetramethyl-1-piperidinyloxy (TEMPO), and 4-hydroxy-2,2,6,6-tetramethyl-1-piperidinyloxy.

Especially preferred mediators are selected from the group consisting of N-hydroxyphthalimide, 1-hydroxy-1H- benzotriazole, violuric acid, N-hydroxyacetanilide, nitrosonaphthols, nitrosopyridinols and their derivatives which have been given above.

Very especially preferred are 3-amino-N-hydroxyphthalimide, 4-amino-N-hydroxyphthalimide, N-hydroxyphthalimide, 3-hydroxy-N-hydroxyphthalimide, 3-methoxy-N-hydroxyphthalimide, 3,4-dimethoxy-N-hydroxyphthalimide, 4,5-dimethoxy-N-hydroxyphthalimide, 3,6-dihydroxy-N-hydroxyphthalimide, 3,6-dimethoxy-N-hydroxyphthalimide, 3-methyl-N-hydroxyphthalimide, 4-methyl-N-hydroxyphthalimide, 3,4-dimethyl-N-hydroxyphthalimide, 3,5-dimethyl-N-hydroxyphthalimide, 3,6-dimethyl-N-hydroxyphthalimide, 3-isopropyl-6-methyl-N-hydroxyphthalimide, 3-nitro-N-hydroxyphthalimide, 4-nitro-N-hydroxyphthalimide, 1-hydroxy-1H-benzotriazole, violuric acid, N-hydroxyacetanilide, 3-nitrosoquinoline-2,4-diol, 2,4-dihydroxy-3-nitrosopyridine, 2,6-dihydroxy-3-nitrosopyridine, 2,4-dinitroso-1,3-dihydroxybenzene, 2-nitroso-1-naphthol-3-sulfonic acid and 1-nitroso-2-naphthol-3,6-disulfonic acid.

The oxidation is preferably carried out in the presence of 0.01 to 10 equivalents, preferably 0.05 to 1 equivalent, especially preferably 0.1 to 0.5 equivalent of one or more of the mediators described, preferably with one or two mediators, especially preferably with one mediator in water.

If appropriate, this is done with addition of 1 to 90 percent by weight, preferably 5 to 30 percent by weight, of a solvent which is at least partially miscible with water. It is preferred to add 1 to 3 organic solvents which are miscible with water as cosolvents. Examples of organic solvents which are miscible with water are ethanol, methanol, isopropanol, ethylene glycol, ethylene glycol monoethyl ether, ethylene glycol monomethyl ether, acetone, acetonitrile, acetamide, tetrahydrofuran, dioxane, DMSO, DMF, sulfolane, methyl acetate, ethyl acetate, formic acid, acetic acid or propionic acid, or any mixtures of these.

The pH of the solution is preferably 2 to 8, especially preferably 4 to 5.

The reactions are preferably carried out at temperatures between 5 and 70° C., especially preferably 35–50° C., and the reaction times are preferably 2 to 100 hours, especially preferably 5 to 50 hours.

Oxidants which are preferably employed are air, oxygen, hydrogen peroxide, organic peroxides, peracids, perborates or persulfates, in each case in combination with enzymes or metal oxides.

The term enzyme for the purposes of the invention also includes enzymatically active proteins or peptides or prosthetic groups of enzymes. Enzymes which can be employed in the multi-component system according to the invention are oxidoreductases of classes 1.1.1 to 1.97 in accordance with the International Enzyme Nomenclature, Committee of the International Union of Biochemistry and Molecular Biology (Enzyme Nomenclature, Academic Press, Inc., 1992, pp. 24–154).

Enzymes of the classes mentioned below are preferably employed:

Enzymes of class 1.1, which embrace all dehydrogenases which act on primary, secondary alcohols and semiacetals and which have, as acceptors $NAD^+$ or $NADP^+$ (subclass 1.1.1), cytochromes (1.1.2), oxygen ($O_2$) (1.1.3), disulfides (1.1.4), quinones (1.1.5) or which have other acceptors (1.1.99).

Especially preferred amongst this class are the enzymes of class 1.1.5 with quinones as the acceptors and the enzymes of class 1.1.3 with oxygen as the acceptor.

Particularly preferred amongst this class is cellobiose: quinone-1-oxidoreductase (1.1.5.1).

Furthermore preferred are enzymes of class 1.2. This enzyme class embraces those enzymes which oxidize aldehydes to the corresponding acids or oxo groups. The acceptors can be NAD+, $NADP_+$ (1.2.1), cytochromes (1.2.2), oxygen (1.2.3), sulfides (1.2.4), iron-sulfur-proteins (1.2.5) or other acceptors (1.2.99).

Especially preferred here are the enzymes of group (1.2.3) with oxygen as the acceptor.

Furthermore preferred are enzymes of class 1.3.

In this class there are compiled enzymes which act on CH—CH groups of the donor.

The corresponding acceptors are $NAD^+$, $NADP^+$ (1.3.1), cytochromes (1.3.2), oxygen (1.3.3), quinones or related compounds (1.3.5), iron-sulfur-proteins (1.3.7) or other acceptors (1.3.99).

Especially preferred is bilirubin oxidase (1.3.3.5).

Again, the enzymes of class (1.3.3) with oxygen as the acceptor and (1.3.5) with quinones etc. as the acceptor are especially preferred here.

Furthermore preferred are enzymes of class 1.4, which act on $CH-NH_2$ groups of the donor.

The corresponding acceptors are $NAD^+$, $NADP^+$ (1.4.1), cytochromes (1.4.2), oxygen (1.4.3), disulfides (1.4.4), iron-sulfur-proteins (1.4.7) or other acceptors (1.4.99).

Here too, especially preferred are enzymes of class 1.4.3 with oxygen as the acceptor.

Furthermore preferred are enzymes of class 1.5, which act on CH—NH groups of the donor. The corresponding acceptors are $NAD^+$, $NADP^+$ (1.5.1), oxygen (1.5.3), disulfides (1.5.4), quinones (1.5.5) or other acceptors (1.5.99).

Again, especially preferred here are enzymes with oxygen ($O_2$) (1.5.3) and with quinones (1.5.5) as the acceptors.

Furthermore preferred are enzymes of class 1.6, which act on NADH or NADPH.

Here, the acceptors are $NADP^+$ (1.6.1), hem proteins (1.6.2), disulfides (1.6.4), quinones (1.6.5), $NO_2$ groups (1.6.6) and a flavine (1.6.8) or some other acceptors (1.6.99).

Especially preferred here are enzymes of class 1.6.5 with quinones as the acceptors.

Furthermore preferred are enzymes of class 1.7, which act on other $NO_2$ compounds as donors and which have cytochromes (1.7.2), oxygen ($O_2$) (1.7.3), iron-sulfur-proteins (1.7.7) or others (1.7.99) as the acceptors.

Especially preferred here is class 1.7.3 with oxygen as the acceptor.

Furthermore preferred are enzymes of class 1.8, which act on sulfur groups as donors and which have $NAD^+$, $NADP^+$ (1.8.1), cytochromes (1.8.2), oxygen ($O_2$) (1.8.3), disulfides (1.8.4), quinones (1.8.5), iron-sulfur-proteins (1.8.7) or others (1.8.99) as the acceptors.

Especially preferred is class 1.8.3 with oxygen ($O_2$) and (1.8.5) with quinones as the acceptors.

Furthermore preferred are enzymes of class 1.9, which act on hem groups as donors and which have oxygen ($_2$) (1.9.3), $NO_2$ compounds (1.9.6) and others (1.9.99) as the acceptors.

Especially preferred here is group 1.9.3 with oxygen ($O_2$) as the acceptor (cytochrome oxidases).

Furthermore preferred are enzymes of class 1.12, which act on hydrogen as the donor.

The acceptors are $NAD^+$ or $NADP^+$ (1.12.1) or others (1.12.99).

Furthermore preferred are enzymes of class 1.13 and 1.14 (oxygenases).

Furthermore preferred enzymes are those of class 1.15, which act on superoxide free radicals as the acceptors.

Especially preferred here is superoxide dismutase (1.15.1.1).

Furthermore preferred are enzymes of class 1.16. NAD$^+$ or NADP$^+$ (1.16.1) or oxygen (O$_2$) (1.16.3) act as the acceptors.

Especially preferred here are enzymes of class 1.16.3.1 (ferroxidase, e.g. ceruloplasmin).

Furthermore preferred enzymes are those which belong to group 1.17 (acts on CH$_2$ groups, which are oxidized to —CHOH—), 1.18 (acts on reduced ferredoxin as donor), 1.19 (acts on reduced flavodoxin as donor) and 1.97 (other oxidoreductases).

Furthermore especially preferred are the enzymes of group 1.11., which act on a peroxide as the acceptor. This single subclass (1.11.1) contains the peroxidases.

Especially preferred here are cytochrome c peroxidases (1.11.1.5), catalase (1.11.1.6), peroxidase (1.11.1.7), iodide peroxidase (1.11.1.8), glutathione peroxidase (1.11.1.9), chloride peroxidase (1.11.1.10), L-ascorbate peroxidase (1.11.1.11), phospholipid hydroperoxide glutathione peroxidase (1.11.1.12), manganese peroxidase (1.12.1.13) and diarylpropane peroxidase (ligninase, lignin peroxidase) (1.11.1.14).

Very especially preferred are enzymes of class 1.10, which act on biphenols and related compounds. They catalyze the oxidation of biphenols and ascorbates. NAD$^+$, NADP$^+$ (1.10.1), cytochromes (1.10.2), oxygen (1.10.3) or others (1.10.99) act as the acceptors.

Amongst these, in turn, especially preferred enzymes are those of class 1.10.3 with oxygen (O$_2$) as the acceptor.

Preferred amongst the enzymes of this class are the enzymes catechol oxidase (tyrosinase) (1.10.3.1), L-ascorbate oxidase (1.10.3.3), o-aminophenol oxidase (1.10.3.4) and laccase (benzenediol: oxygen oxidoreductase) (1.10.3.2), the laccases (benzenediol: oxygen oxidoreductase) (1.10.3.2) being particularly preferred.

The abovementioned enzymes are commercially available or can be obtained by standard processes. Organisms which are suitable for producing the enzymes are, for example, plants, animal cells, bacteria and fungi. In principle, naturally occurring and genetically altered organisms may be enzyme producers. Equally, parts of single- or many-celled organisms are conceivable as enzyme producers, above all cell cultures.

Examples of organisms which are used for the particularly preferred enzymes, such as those from group 1.11.1, but mainly 1.10.3, and in particular for the production of laccases are fungi that cause white rot such as Pleurotus, Phlebia and Trametes.

Preferred amongst the metal oxides employed as oxidants are those with a solubility of less than 1 g/l in the reaction medium.

The following are preferred: bismuth(III) oxide, iridium (III) oxide, cerium(IV) oxide, cobalt(II) oxide, cobalt(III) oxide, iron(III) oxide, manganese(IV) oxide, tin(IV) oxide, niobium(V) oxide, antimony(V) oxide, indium(III) oxide, mercury(II) oxide, lead(IV) oxide, silver(I) oxide, copper(II) oxide, palladium(II) oxide.

The following are especially preferred: lead(IV) oxide, manganese(IV) oxide, silver(I) oxide, copper(II) oxide, palladium(II) oxide.

The process according to the invention allows aromatic or heteroaromatic aldehydes and ketones to be prepared from the corresponding methyl or methylene compounds under mild reaction conditions.

The reaction is preferably carried out in water, if appropriate with addition of a cosolvent as solubilizer, and is therefore especially inexpensive.

The reaction solution is worked up in a simple manner, for example by extraction.

The mediators used can be employed catalytically. Aromatics which are substituted by electron donors react especially fast. The high selectivity is shown with reference to the oxidation of o-xylene. Here, the first methyl group is oxidized much faster, which allows o-tolyl aldehyde to be synthesized.

DETAILED DESCRIPTION OF PREFERRED EMBODIMENTS

Other objects and features of the present invention will become apparent from the following detailed description considered in connection with the accompanying examples. It should be understood, however, that this is designed for the purpose of illustration only and not as a definition of the limits of the invention.

EXAMPLE 1

22 ml of a dipotassium hydrogen phosphate/citric acid buffer solution of pH 4.5 (prepared by titrating a 0.2 M potassium dihydrogen phosphate solution with a 0.1 M citric acid solution and diluting to ¼) were treated at 45° C. with 243 mg (1.60 mmol) of 3,4-dimethoxytoluene in 1 ml of ethanol. 0.180 minmol of a mediator (Table 1) was added with stirring. After approx. 10 minutes, the mixture was treated with 5 ml of an aqueous solution of 2 mg/ml laccase from Trametes versicolor (specific activity: approx. 18 IU/mg, defined with ABTS as substrate). After a reaction time of 22 hours with exposure to air, the reaction solution was extracted with chloroform and examined by NMR spectroscopy and gas chromatography. Yields of 3,4-dimethoxybenzaldehyde and 3,4dimethoxybenzyl alcohol, see Table 1.

TABLE 1

Conversion of 3,4-dimethoxytoluene with laccase and a variety of mediators (cosolvent: ethanol)

| Mediator (0.11 equ.) | Aldehyde (%) | Alcohol (%) |
| --- | --- | --- |
| 1-hydroxy-1H-benzotriazole | 85 | 14 |
| N-hydroxyphthalimide (=HPI) | 9 | 4 |
| 3,6-dihydroxy-HPI | 0.2 | 0.5 |
| 3,4-dimethoxy-HPI | 26 | 7 |
| 4,5-dimethoxy-HPI | 27 | 6 |
| 3,6-dimethoxy-HPI | 17 | 4 |
| 3,5-dimethyl-HPI | 33 | 7 |
| 3-isopropyl-6-methyl-HPI | 90 | 10 |
| 3-methyl-HPI | 81 | 7 |
| 4-methyl-HPI | 84 | 11 |
| 3-amino-HPI | 91 | 7 |

EXAMPLE 2

195 mg (1.60 mmol) of 4-methylanisole were reacted analogously to Example 1 in the presence of 32.1 mg (0.180 mmol) of 3-amino-N-hydroxyphthalimide. After a reaction time of 22 hours, the reaction solution was extracted with chloroform and examined by NMR spectroscopy and gas chromatography. Yield 61% of 4-methoxybenzaldehyde (approx. 90%, based on conversion).

EXAMPLE 3

195 mg (1.60 mmol) of 4-methylanisole were reacted analogously to Example 1 in the presence of 24.3 mg (0.180 mmol) of 1-hydroxy-1H-benzotriazole. After a reaction time of 22 hours, the reaction solution was extracted with chloroform and examined by NMR spectroscopy. Yield 48% of 4-methoxybenzaldehyde (approx. 90%, based on conversion).

EXAMPLE 4

172 mg (1.60 mmol) of 4-toluidine were reacted analogously to Example 1 in the presence of 32.1 mg (0.180 mmol) of 3-amino-N-hydroxyphthalimide. After a reaction time of 22 hours, the reaction solution was brought to pH 8 with 2M NaOH, extracted with chloroform and examined by NMR spectroscopy. Yield 62% of 4-aminobenzaldehyde.

EXAMPLE 5

170 mg (1.60 mmol) of o-xylene were reacted analogously to Example 1 in the presence of 32.1 mg (0.180 mmol) of 3-amino-N-hydroxyphthalimide. After a reaction time of 4 hours and 18 hours, a further 32.1 mg (0.180 mmol) of 3-amino-N-hydroxyphthalimide were added in each case, and, after a total of 30 hours, the reaction solution was extracted with chloroform and examined by NMR spectroscopy. Yield 30% of 2-methylbenzaldehyde and 7% of 2-methylbenzyl alcohol.

EXAMPLE 6

188 mg (1.60 mmol) of 4-tolunitrile were reacted analogously to Example 1 in the presence of 32.1 mg (0.180 mmol) of 3-amino-N-hydroxyphthalimide. After a reaction time of 22 hours, the reaction solution was extracted with chloroform and examined by NMR spectroscopy. Yield 10%.

EXAMPLE 7

212 mg (1.60 mmol) of 1,2,3,4-tetrahydronaphthalene in 1.1 ml of acetone were reacted analogously to Example 1 with 71 mg (0.53 mmol) of 1-hydroxy-1H-benzotriazole in 3 ml of acetone and 15 ml of an aqueous solution of 2 mg/ml laccase from Trametes versicolor. After a reaction time of 24 hours, the reaction solution was extracted with chloroform and examined by NMR spectroscopy. Yield 42% of 1-tetralone and 6% of 5-hydroxytetralin (approx. 90% yield of 1-tetralone based on conversion).

EXAMPLE 8

1-ethylbenzene was reacted analogously to Example 1 with 0.22 equivalent of 1-hydroxy-1H-benzotriazole and 10 ml of a solution of 2 mg/ml laccase. After a reaction time of 24 hours, the reaction solution was extracted with chloroform and examined by NMR spectroscopy. Yield 42% of acetophenone, 34% of 1-phenylethanol, 24% of unreacted acetophenone.

EXAMPLE 9

259 mg (1.60 mmol) of 6-methoxy-1,2,3,4-tetrahydronaphthalene in 1.1 ml of solvent were reacted analogously to Example 1 with a variety of mediators and laccase (see Table 2). After a reaction time of 24 hours, the reaction solution was extracted with chloroform and examined by NMR spectroscopy. Yields of 6-methoxy-1-tetralone and 6-methoxy-1-hydroxy-1,2,3,4-tetrahydronaphthalene, see Table 2.

Table 2

Oxidation of 6-methoxy-1,2,3,4-tetrahydronaphthalene to 6-methoxy-1-tetralone (HOBT: 1-hydroxy-1H-benzotriazole, 4-methyl-HPI: 4-methyl-N-hydroxyphthalimide)

| Mediator (equiv., cosolvent) | Laccase (U/mmol) | %1 | %2 |
|---|---|---|---|
| HOBT (0.11, ethanol) | 113 | 29 | 7 |
| HOBT (0.22, ethanol) | 113 | 52 | 13 |
| HOBT (0.33, ethanol) | 113 | 60 | 12 |
| HOBT (0.11, ethanol) | 339 | 51 | 11 |
| HOBT (0.33, ethanol) | 339 | 95 | 2 |
| HOBT (0.11, ethanol)[a] | 113[a] | 39 | 3 |
| HOBT (0.11, acetone) | 113 | 35 | 7 |
| HOBT (0.22, acetone)[b] | 226[b] | 51[c] | 8 |
| HPI (0.22/acetone)[b] | 226[b] | 21[d] | 8 |
| 4-methyl-HPI (0.11, ethanol) | 113 | 8 | 8 |
| 4-methyl-HPI (0.22, ethanol) | 113 | 32 | 8 |
| 4-methyl-HPI (0.11, ethanol) | 339 | 59 | 5 |
| 4-methyl-HPI (0.33, ethanol) | 339 | 92 | 3 |
| 4-methyl-HPI (0.11, ethanol)[a] | 113[a] | 36 | 4 |
| 4-methyl-HPI (0.11, acetone) | 113 | 31 | 6 |
| 3-amino-HPI (0.11, ethanol) | 113 | 37 | 6 |
| 3-amino-HPI (0.22, ethanol) | 113 | 32 | 10 |
| 3-N,N-dimethylamino-HPI (0.11, ethanol) | 113 | 43 | 13 |

[a] Addition in 3 portions,
[b] addition in 5 portions,
[c] 24% of unreacted 1,2,3,4-tetrahydronaphthalene,
[d] 58% of unreacted 1,2,3,4-tetrahydronaphthalene.

EXAMPLE 10

22 ml of a dipotassium hydrogen phosphate/citric acid buffer solution of pH 4.5 (prepared by titrating a 0.2 M potassium dihydrogen phosphate solution with a 0.1 M citric acid solution and diluting to ¼) were treated at 45° C. with 243 mg (1.60 mmol) of 3,4-dimethoxytoluene in 1 ml of ethanol. 32.1 mg (0.180 mmol) of 3-amino-N-hydroxyphthalimide were added with stirring. After approx. 10 minutes, 950 mg (3.97 mmol) of lead dioxide were added, and the mixture was stirred for 22 hours at 45° C. in a sealed flask. HPLC analysis of the reaction mixture revealed 9% of 3,4-dimethoxybenzaldehyde and 28% of 3,4-dimethoxybenzyl alcohol.

EXAMPLE 11

243 mg (1.60 mmol) of 3,4-dimethoxytoluene were reacted analogously to Example 8 with 32.1 mg (0.180 mmol) of 3-amino-N-hydroxyphthalimide and 346 mg (3.98 mmol) of manganese dioxide. HPLC analysis after a reaction time of 22 hours revealed 13% of 3,4-dimethoxybenzaldehyde and 19% of 3,4-dimethoxybenzyl alcohol.

EXAMPLE 12

Following the protocol of Potthast et al. (J. Org. Chem. 1995, 60, 4320), 13.7 mg (0.100 mmol) of 4-nitrotoluene in 0.1 ml of THF were added to a solution of 0.55 mg (0.010 mmol) of ABTS in 0.5 ml of acetate buffer, and the stirred mixture was flushed for 1 minute with oxygen. After addition of 0.10 ml of laccase stock solution (Mercian, laccase activity 95 IU, based on the conversion of 4-hydroxymandelic acid as substrate), the reaction mixture turned deep bluish-green and was stirred for 23 hours at room temperature. The reaction mixture was subsequently again flushed for 1 minute with oxygen and the reaction was continued for 8 hours at 40° C., and this procedure was repeated twice more. Besides unreacted 4-nitrotoluene, 4-nitrobenzaldehyde was no longer detectable when examining the reaction solution by gas chromatography (detection limit approx. 0.02%).

EXAMPLE 13

Following the protocol of Potthast et al. (J. Org. Chem. 1995, 60, 4320), 15.2 mg (0.100 mmol) of 3,4-dimethoxytoluene in 0.1 ml of THF were added to a solution of 0.55 mg (0.010 mmol) of ABTS in 0.5 ml of acetate buffer, analogously to Example 8, and the stirred mixture was flushed for 1 minute with oxygen. After addition of 0.10 ml of laccase stock solution (see Example 10), the reaction mixture turned deep bluish-green and was stirred for 8 hours at room temperature. The reaction mixture was subsequently again flushed for 1 minute with oxygen and the reaction was continued for 16 hours at room temperature. The mixture was again flushed with oxygen and the reaction was continued for 7 hours at 40° C. Examination of the reaction solution by gas chromatography revealed 0.3% of 3,4-dimethoxybenzaldehyde.

While several embodiments of the present invention have been shown and described, it is to be understood that many changes and modifications may be made thereunto without departing from the spirit and scope of the invention as defined in the appended claims.

What is claimed is:

1. A process for the preparation of a heteroaryl aldehyde and a heteroaryl ketone comprising
   reacting a compound selected from the group consisting of heteroarylmethyl, and heteroarylmethylene with an oxidant and with the aid of a mediator in a reaction medium,
     wherein the mediator is selected from the group consisting of the aliphatic, heterocyclic and aromatic NO, or NOH containing compounds.

2. A process as claimed in 1, wherein the aldehyde and the ketone are each a compound of the formula 1, and the methyl compound and the methylene compound are each a compound of the formula 2

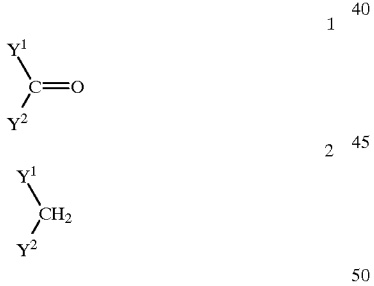

where $Y^1$ and $Y^2$ can be identical or different and are radicals having up to 20 C atoms and up to 6 rings and at least one of the radicals $Y^1$ or $Y^2$ is heteroaryl, and $Y^1$ and $Y^2$ may also be part of a ring system; and with the proviso that whenever the compound of formula 1 is an aldehyde, $Y^1$ or $Y^2$ is hydrogen.

3. A process as claimed in claim 2, wherein $Y^1$ is the following: heteroaromatic ring or a ring system having up to 6 rings and up to 20 C atoms, whose ring members can be replaced by O, S or N atoms, or an anthraquinonyl radical, it being possible for the heteroaromatic radical $Y^1$ to be mono- to hexasubstituted,
   it being possible for the substituents to be identical or different and to have the meaning of OH, a linear, branched or cyclic $C_1$–$C_{12}$-alkyl radical, it being possible for adjacent alkyl groups to form a 5-, 6- or 7-membered ring via a methylene group, or a linear or branched $C_1$–$C_{12}$-oxyalkyl or thioalkyl radical, it being possible for adjacent substituents to form a 5-, 6- or 7-membered ring via a methylene group, a $H_2N$— or a linear or branched $C_1$–$C_{12}$—N-alkylamino, a linear or branched $C_1$–$C_{12}$—N,N-dialkylamino group, NC—, $O_2N$—, halogen, HOOC—, $HO_3S$—, OHC—, $H_2N$—COO—, $H_2N$—CO—, $H_2N$—CO—NH—, or a linear, branched or cyclic $C_1$–$C_{12}$—OCO—, $C_1$–$C_{12}$—COO—, $C_1$–$C_{12}$—CO—, $C_1$–$C_{12}$—NHCO—, $C_1$–$C_{12}$—NHCONH—, $(C_1$–$C_{12})_2$NCO—, $C_1$–$C_{12}$—CONH— group, or a linear or branched $C_1$–$C_{12}$—OSO_2—, $C_1$–$C_{12}$—NH—SO_2—, or $(C_1$–$C_{12})_2$N—SO_2— group, or a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-OSO_2— or phenyl-NH—SO_2— group whose phenyl radicals can be mono- to pentasubstituted, it being possible for the substituents to be identical or different and to have the meaning of OH, a linear, branched or cyclic $C_1$–$C_{12}$-alkyl radical, it being possible for adjacent alkyl groups to form a 5-, 6- or 7-membered ring via a methylene group, or of a linear or branched $C_1$–$C_{12}$-oxyalkyl or thioalkyl radical, it being possible for adjacent substituents to form a 5-, 6- or 7-membered ring via a methylene group, a $H_2N$— or a linear or branched $C_1$–$C_{12}$—N-alkylamino, a linear or branched $C_1$–$C_{12}$—N,N-dialkylamino group, NC—, $O_2N$—, halogen, HOOC—, $HO_3S$—, OHC—, $H_2N$—COO—, $H_2N$—CO—, $H_2N$—CO—NH—, or a linear, branched or cyclic $C_1$–$C_{12}$—OCO—, $C_1$–$C_{12}$—COO—, $C_1$–$C_{12}$—CO—, $C_1$–$C_{12}$—NHCO—, $C_1$–$C_{12}$—NHCONH—, $(C_1$–$C_{12})_2$NCO—, $C_1$–$C_{12}$—CONH—, or of a linear or branched $C_1$–$C_{12}$—OSO_2—, $C_1$–$C_{12}$—NH—SO_2— or $(C_1$–$C_{12})_2$N—SO_2— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-OSO_2— or phenyl-NH—SO_2— group or an optionally mono- to trisubstituted vinyl radical or optionally substituted ethynyl radical, in which the substituents can be identical or different and have the meaning of hydrogen, linear, branched or cyclic $C_1$–$C_{12}$-alkyl radical where one or more methylene groups can be replaced individually by CHOH, CO, O, S, NH or by a linear or branched $C_1$–$C_{12}$—N-alkylamine radical, or in which the vinyl group forms part of a ring or ring system, and $Y^2$ is the following: hydrogen, linear, branched or cyclic $C_1$–$C_{12}$-alkyl radical where one or more methylene groups can be replaced individually by CHOH, CO, O, S, NH or by a linear or branched $C_1$–$C_{12}$—N-alkylamine radical, or heteroaromatic ring or ring system having up to 6 rings and up to 20 C atoms, whose ring members can be replaced by O, S or N atoms, or anthraquinonyl radical, or an optionally mono- to trisubstituted vinyl radical or optionally substituted ethynyl radical, in which the substituents can be identical or different and have the meaning of hydrogen, linear, branched or cyclic $C_1$–$C_{12}$-alkyl radical where one or more methylene groups can be replaced individually by CHOH, CO, O, S, NH or by a linear or branched $C_1$–$C_{12}$—N-alkylamine radical, or in which the vinyl group forms part of a ring or ring system, it furthermore being possible for the radicals $Y^1$ and $Y^2$ to be linked via a methylene group or an ether group or via an amino group which is optionally substituted by a linear, branched or cyclic $C_1$–$C_{12}$-alkyl radical.

4. A process as claimed in claim 2, wherein $Y^1$ is the following: 5-, 6- or 7-membered heteroaromatic ring which can be fused to one or two further aromatic rings and where one to four C atoms can be replaced by O, S or N atoms, or an anthraquinonyl radical, it being possible for $Y^1$ to be mono- to tetrasubstituted, it being possible for the substituents to be identical or different and to have the meaning of OH, a linear, branched or cyclic $C_1$–$C_6$-alkyl radical, it being possible for adjacent alkyl groups to form a 5- or 6-membered ring via a methylene group, or a linear or branched $C_1$–$C_6$-oxyalkyl or -thioalkyl radical, it being possible for adjacent substituents to form a 5- or 6-membered ring via a methylene group, of a $H_2N$—, or a linear or branched $C_1$–$C_6$—N-alkylamino, a linear or branched $C_1$–$C_3$—N,N-dialkylamino group, NC—, $O_2N$—, halogen, HOOC—, $HO_3S$—, OHC—, $H_2N$—COO—, $H_2N$—CO—, $H_2N$—CO—NH—, or a linear, branched or cyclic $C_1$–$C_6$—OCO—, $C_1$–$C_6$—COO—, $C_1$–$C_6$—CO—, $C_1$–$C_6$—NHCO—, $C_1$–$C_6$—NHCONH—, $(C_1$–$C_6)_2NCO$—, $C_1$–$C_6$—CONH—, or of a linear or branched $C_1$–$C_6$—$OSO_2$—, $C_1$–$C_6$—NH—$SO_2$— or $(C_1$–$C_3)_2N$—$SO_2$— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-$OSO_2$— or phenyl-NH—SO2— group, it being possible for the phenyl radicals to be mono- to trisubstituted, it being possible for the substituents to be identical or different and to have the meaning of OH, a linear, branched or cyclic $C_1$–$C_6$-alkyl radical, it being possible for adjacent alkyl groups to form a 5- or 6-membered ring via a methylene group, or a linear or branched $C_1$–$C_6$-oxyalkyl or -thioalkyl radical, it being possible for adjacent substituents to form a 5- or 6-membered ring via a methylene group, of a $H_2N$—, or a linear or branched $C_1$–$C_6$—N-alkylamino, a linear or branched $C_1$–$C_6$—N,N-dialkylamino group, NC—, $O_2N$—, halogen, HOOC—, $HO_3S$—, OHC—, $H_2N$—COO—, $H_2N$—CO—, $H_2N$—CO—NH—, or a linear, branched or cyclic $C_1$–$C_6$—OCO—, $C_1$–$C_6$—COO—, $C_1$–$C_6$—CO—, $C_1$–$C_6$—NHCO—, $C_1$–$C_6$—NHCONH—, $(C_1$–$C_6)_2NCO$—, $C_1$–$C_6$—CONH—, or of a linear or branched $C_1$–$C_6$—$OSO_2$—, $C_1$–$C_6$—NH—$SO_2$— or $(C_1$–$C_3)_2N$—$SO_2$— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-$OSO_2$— or phenyl-NH—$SO_2$— group, or an optionally mono- to trisubstituted vinyl radical or optionally substituted ethynyl radical, it being possible for the substituents to be identical or different and to be hydrogen or linear, branched, or cyclic $C_1$–$C_6$-alkyl radical where one or two methylene groups can be replaced individually by CHOH, CO, O, S, NH or by a linear or branched $C_1$–$C_6$—N-alkylamine radical, or in which the vinyl group forms part of a 5- or 6-membered ring or of a ring system, and $Y^2$ is the following: hydrogen or linear, branched or cyclic $C_1$–$C_6$-alkyl radical where one or two methylene groups can be replaced individually by CHOH, CO, O, S, NH or by a linear or branched $C_1$–$C_6$—N-alkylamine radical, or a 5-, 6- or 7-membered heteroaromatic ring which can be fused to one or two further aromatic rings and where one to four C atoms can be replaced by O, S or N atoms, or an anthraquinonyl radical, or an optionally mono- to trisubstituted vinyl radical, or an optionally substituted ethynyl radical, it being possible for the substituents to be identical or different and to be hydrogen or linear, branched, or cyclic $C_1$–$C_6$-alkyl radical where one or two methylene groups can be replaced individually by CHOH, CO, O, S, NH or by a linear or branched $C_1$–$C_6$—N-alkylamine radical, or in which the vinyl group forms part of a 5- or 6-membered ring or of a ring system.

5. A process as claimed in claim 2, wherein $Y^1$ is the following: azulenyl, anthraquinonyl, furyl, pyrrolyl, thienyl, benzofuranyl, isobenzofuranyl, benzothiyl, isobenzothienyl, indolyl, isoindolyl, indolizinyl, pyrazolyl, imidazolyl, oxazolyl, thiazolyl, isoxazolyl, isothiazolyl, indazolyl, carbazolyl, benzotriazolyl, purinyl, pyridyl, pyridazinyl, pyrimidyl, pyrazinyl, quinolinyl, isoquinolinyl, quinoxalinyl, quinazolinyl, cinnolinyl, phenanthridinyl, acridinyl, 1,10-phenanthrolinyl, phenazinyl, phenothiazinyl, phenoxazinyl, it being possible for $Y^1$ to be mono- to trisubstituted, it being possible for the substituents to be identical or different and to have the meaning of OH, a linear $C_1$–$C_6$-alkyl radical, it being possible for adjacent alkyl groups to form a 5- or 6-membered ring via a methylene group, or of a linear $C_1$–$C_6$-oxyalkyl radical, it being possible for adjacent substituents to form a 5- or 6-membered ring via a methylene group, a $H_2N$—, or a linear $C_1$–$C_6$—N-alkylamino, a linear $C_1$–$C_3$—N,N-dialkylamino group, NC—, $O_2N$—, halogen, HOOC—, $HO_3S$—, OHC—, $H_2N$—COO—, $H_2N$—CO—, $H_2N$—CO—NH—, or a linear $C_1$–$C_4$—OCO—, $C_1$–$C_4$—COO—, $C_1$–$C_4$—CO—, $C_1$–$C_4$—NHCO—, $(C_1$–$C_4)_2NCO$—, $C_1$–$C_4$—CONH—, $C_1$–$C_4$—NHCONH—, or $C_1$–$C_4$—$OSO_2$—, $C_1$–$C_4$—NH—$SO_2$— or $(C_1$–$C_3)_2N$—$SO_2$— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-$OSO_2$— or phenyl-NH—$SO_2$— group, it being possible for the phenyl radicals to be mono- to trisubstituted, it being possible for the substituents to be identical or different and to have the meaning of OH, a linear $C_1$–$C_6$-alkyl radical, it being possible for adjacent alkyl groups to form a 5- or 6-membered ring via a methylene group, or of a linear $C_1$–$C_6$-oxyalkyl radical, it being possible for adjacent substituents to form a 5- or 6-membered ring via a methylene group, a $H_2N$—, or a linear $C_1$–$C_6$—N-alkylamino, a linear $C_1$–$C_3$—N,N-dialkylamino group, NC—, $O_2N$—, halogen, HOOC—, $HO_3S$—, OHC—, $H_2N$—COO—, $H_2N$—CO—, $H_2N$—CO—NH—, or a linear $C_1$–$C_4$—OCO—, $C_1$–$C_4$—COO—, $C_1$–$C_4$—CO—, $C_1$–$C_4$—NHCO—, $(C_1$–$C_4)_2NCO$—, $C_1$–$C_4$—CONH—, $C_1$–$C_4$—NHCONH—, or $C_1$–$C_4$—$OSO_2$—, $C_1$–$C_4$—NH—$SO_2$— or $(C_1$–$C_3)_2N$—$SO_2$— group, or of a phenyl, diphenylmethyl, phenyl-CH=CH—, phenyl-N=N—, phenyl-N=CH—, phenyl-CH=N—, phenoxy, phenyl-NH—, phenyl-O—CO—, phenyl-CO—, phenyl-NHCO—, phenyl-CONH—, phenyl-NHCONH—, phenyl-$OSO_2$— or phenyl-NH—$SO_2$— group or an optionally mono- to trisubstituted vinyl radical, or optionally substituted ethynyl radical, in which the substituents can be identical or different and are hydrogen or linear $C_1$–$C_6$-alkyl radical where one or two methylene groups can be replaced individually by CHOH, CO, O, S, NH or by a linear or branched $C_1$–$C_6$-N-alkylamine radical, or in which the vinyl group forms part of a 5- or 6-membered ring or of a ring system, and $Y^2$ is the following: hydrogen or a linear $C_1$–$C_6$-alkyl radical where one or two methylene groups can be replaced individually by CHOH, CO, O, S, NH or by a linear or branched $C_1$–$C_6$—N-alkylamine radical, or is azulenyl, anthraquinonyl, furyl, pyrrolyl, thienyl, benzofuranyl, isobenzofuranyl, benzothiyl, isobenzothienyl, indolyl, isoindolyl, indolizinyl, pyrazolyl, imidazolyl, oxazolyl, thiazolyl, isoxazolyl, isothiazolyl, indazolyl, carbazolyl, benzotriazolyl, purinyl, pyridyl, pyridazinyl, pyrimidyl, pyrazinyl, quinolinyl, isoquinolinyl, quinoxalinyl, quinazolinyl, cinnolinyl, phenanthridinyl, acridinyl, 1,10-phenanthrolinyl, phenazinyl, phenothiazinyl, phenoxazinyl, or an optionally mono- to trisubstituted vinyl radical, or optionally substituted ethynyl radical, in which the substituents can be identical or different and are hydrogen or linear $C_1$–$C_6$-alkyl radical where one or two methylene groups can be replaced individually by CHOH, CO, O, S, NH or by a linear or branched $C_1$–$C_6$—N-alkylamine radical, or in which the vinyl group forms part of a 5- or 6-membered ring or of a ring system, where, furthermore, the radicals $Y^1$ and $Y^2$ can be linked via a methylene group or an ether group or via an amino group which is optionally substituted by a methyl, ethyl, - or iso-propyl radical, the linkage resulting in 5- or 6-membered rings.

6. A process as claimed in claim 1,
   wherein the mediator is at least one compound selected from the group consisting of N-hydroxyphthalimide, 1-hydroxy-1H-benzotriazole, violuric acid, N-hydroxyacetanilide, nitrosonaphthols, nitrosopyridinols and the derivatives thereof.

7. A process as claimed in claim 1,
   wherein the mediator is at least one compound selected from the group consisting of 3-amino-N-hydroxyphthalimide, 4-amino-N-hydroxyphthalimide, N-hydroxyphthalimide, 3-hydroxy-N-hydroxyphthallimide, 3-methoxy-N-hydroxyphthalimide, 3,4-dimethoxy-N-hydroxyphthalimide, 4,5-dimethoxy-N-hydroxyphthalimide, 3,6-dihydroxy-N-hydroxyphthalimide, 3,6-dimethoxy-N-hydroxyphthalimide, 3-methyl-N-hydroxyphthalimide, 4-methyl-N-hydroxyphthalimide, 3,4-dimethyl-N-hydroxyphthalimide, 3,5-dimethyl-N-hydroxyphthalimide, 3,6-dimethyl-N-hydroxyphthalimide, 3-isopropyl-6-methyl-N-hydroxyphthalimide, 3-nitro-N-hydroxyphthalimide, 4-nitro-N-hydroxy-phthalimide, 1-hydroxy-1H-benzotriazole, violuric acid and N-hydroxyacetanilide, 3-nitrosoquinoline-2,4-diol, 2,4-dihydroxy-3-nitrosopyridine, 2,6-dihydroxy-3-nitrosopyridine, 2,4-dinitroso-1,3-dihydroxybenzene, 2-nitroso-1-naphthol-4-sulfonic acid and 1-nitroso-2-naphthol-3,6-disulfonic acid.

8. A process as claimed in claim 1,
   wherein the oxidant is selected from the group consisting of air, oxygen, hydrogen peroxide, an organic peroxide, a peracid, a perborate and a persulfate with each oxidant in combination with an enzyme.

9. A process as claimed in claim 8, wherein the oxidant is selected from the group consisting of air and oxygen in combination with laccase.

10. A process as claimed in claim 1, wherein the oxidant is a metal oxide with a solubility of less than 1 g/l in the reaction medium.

11. A process as claimed in claim 1, further comprising adding a cosolvent comprising water with one to three solvents which are at least partially miscible with water.

\* \* \* \* \*